US006475361B1

(12) United States Patent
Merenkova et al.

(10) Patent No.: US 6,475,361 B1
(45) Date of Patent: Nov. 5, 2002

(54) CAPILLARY ELECTROPHORESIS APPARATUS HAVING FILLING/REFILLING SYSTEM AND METHODS FOR USE THEREOF

(75) Inventors: Irena N. Merenkova; Maxim Brevnov, both of Moscow (RU)

(73) Assignee: Tetragen SA, Moscow (RU)

( * ) Notice: Subject to any disclaimer, the term of this patent is extended or adjusted under 35 U.S.C. 154(b) by 0 days.

(21) Appl. No.: 09/378,561

(22) Filed: Aug. 19, 1999

Related U.S. Application Data

(63) Continuation-in-part of application No. 09/027,426, filed on Feb. 20, 1998, now Pat. No. 6,103,083.

(51) Int. Cl.[7] .............................................. G01N 27/26
(52) U.S. Cl. ..................... 204/451; 204/455; 204/601; 204/605
(58) Field of Search ................................ 204/451, 455, 204/601, 605

(56) References Cited

U.S. PATENT DOCUMENTS

| 3,980,891 A | 9/1976 | Slaker |
| 4,374,723 A | 2/1983 | Vesterberg |

(List continued on next page.)

FOREIGN PATENT DOCUMENTS

| EP | 0 314 045 A2 | 10/1988 |
| EP | 0 497 480 A1 | 1/1992 |
| EP | 0 533 301 A1 | 3/1993 |
| EP | 0 723 149 A2 | 1/1996 |
| WO | WO 94/29712 | 12/1994 |
| WO | WO 96/13716 | 5/1996 |
| WO | WO 96/36872 | 11/1996 |
| WO | WO 97 08545 A | 3/1997 |
| WO | WO 99 00664 A | 1/1999 |

OTHER PUBLICATIONS

Clark, et al., "High–Speed Parallel Separation of DNA Restriction Fragments Using Capillary Array Electrophoresis[1]", Analytical Biochemistry, 215:163–170 (1993). Apr.

Huang, et al., "Capillary Array Electrophoresis Using Laser– Excited Confocal Fluorescence Detection", Anal. Chem. 1992, 64, 967–972. Apr.

Quesada, et al., "High–Sensitivity DNA Detection with a Laser–Excited Confocal Fluorescence Gel Scanner", 616 BioTechniques, vol. 10, No. 5 (1991).

Scherer, et al., "Ultra–high throughput rotary capillary array electrophoresis scanner for fluorescent DNA sequencing and analysis", Electrophoresis 1999, 20, 1508–1517.

(List continued on next page.)

Primary Examiner—T. Tung
Assistant Examiner—Alex Noguerola
(74) Attorney, Agent, or Firm—Knobbe, Martens, Olson & Bear, LLP

(57) ABSTRACT

The present invention relates to an electrophoresis apparatus having a filling/refilling system and methods of using the same. The electrophoresis apparatus comprises a first buffer chamber comprising a solid portion, at least one inlet channel in said solid portion, and at least one outlet channel in said solid portion, wherein said at least one inlet channel is in fluid communication with at least one inlet port, said at least one outlet channel is in fluid communication with at least one outlet port and said at least one inlet channel is in fluid communication with said at least one outlet channel. The electrophoresis apparatus also comprises a plurality of capillaries having first ends, second ends, and intermediate portions disposed between said first ends and said second ends, wherein said first ends extend into said first buffer chamber and are in fluid communication with said at least one inlet channel and said at least one outlet channel.

55 Claims, 12 Drawing Sheets

U.S. PATENT DOCUMENTS

| | | |
|---|---|---|
| 4,375,401 A | 3/1983 | Catsimpoolas |
| 4,675,095 A | 6/1987 | Kambara et al. |
| 4,811,218 A | 3/1989 | Hunkapiller et al. |
| 4,832,815 A | 5/1989 | Kambara et al. |
| 4,879,012 A | 11/1989 | Kambara et al. |
| 4,930,893 A | 6/1990 | Manian |
| 5,062,294 A | 11/1991 | Iwata |
| 5,091,652 A | 2/1992 | Mathies et al. |
| 5,192,412 A | 3/1993 | Kambara et al. |
| 5,274,240 A | 12/1993 | Mathies et al. |
| 5,324,401 A | 6/1994 | Yeung et al. |
| 5,340,747 A | 8/1994 | Eden |
| 5,413,686 A | 5/1995 | Klein et al. |
| 5,439,578 A | 8/1995 | Dovichi et al. |
| 5,483,075 A | 1/1996 | Smith et al. |
| 5,498,324 A | 3/1996 | Yeung et al. |
| 5,560,811 A | 10/1996 | Briggs et al. |
| 5,597,468 A | 1/1997 | Lauer et al. |
| 5,730,850 A | 3/1998 | Kambara et al. |
| 5,833,827 A | 11/1998 | Anazawa et al. |
| 5,885,430 A | 3/1999 | Kernan et al. |
| 5,916,428 A * | 6/1999 | Kane et al. .................. 204/601 |

OTHER PUBLICATIONS

Swerdlow, H., et al., "Three DNA Sequencing Methods Using Capillary Gel Electrophoresis and Laser–Induced Fluorescence", Anal. Chem. 1991, 63, 2835–2841. Dec.

Takahashi, et al., "Multiple Sheath–Flow Gel Capillary–Array Electrophoresis for Multicolor Fluorescent DNA Detection", Anal. Chem., 66(7):1021–1026 (1994). Apr.

Ueno, et al., "Simultaneous Monitoring of DNA Fragments Separated by Electrophoresis in a Multiplexed Array of 100 Capillaries", Anal. Chem., 66(9):1424–1431 (1994). May.

* cited by examiner

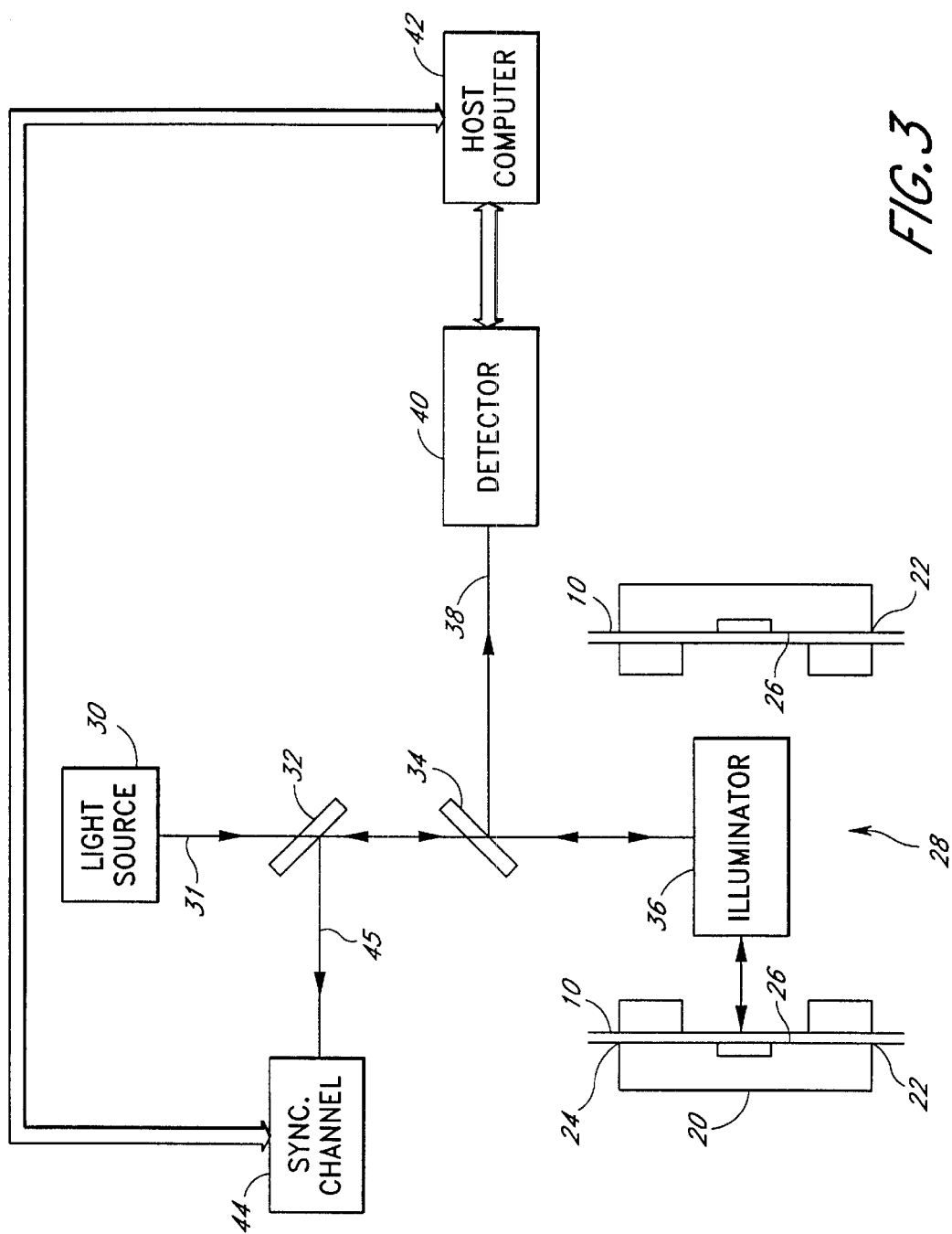

CAPILLARY ELECTROPHORESIS APPARATUS HAVING FILLING/REFILLING SYSTEM AND METHODS FOR USE THEREOF

RELATED APPLICATIONS

The present application is a continuation-in-part of U.S. patent application Ser. No. 09/027,426, filed Feb. 20, 1998, now U.S. Pat. No. 6,103,083 the disclosure of which is incorporated herein by reference in its entirety.

BACKGROUND OF THE INVENTION

Recent advances in molecular biology have greatly accelerated the rate at which genes can be cloned and characterized, rendering determination of the complete genomic sequence of an organism an attainable goal. Accordingly, large scale genomic sequencing efforts for several organisms including bacteria, yeast, and nematodes have already yielded extensive genomic sequence information. Recently, the Human Genome Project, an ambitious project to obtain the entire sequence of the human genome, has commenced. The Human Genome Project paves the way for an even more ambitious project sometimes referred to as the Human Genome Diversity Project, a project aimed at identifying and characterizing allelic differences between humans which manifest themselves in a phenotypically important manner. For example, some allelic variations may be the source of debilitating diseases such as sickle cell anemia or neoplastic diseases.

With cloning techniques well developed, the rate at which information can be extracted from the cloned DNA becomes a limiting factor in determining the genomic sequence of an organism. Accordingly, advances in automated sequencing will reduce the cost and time required to sequence the genomes of model organisms.

For example, in order to sequence the 3 billion nucleotides in the human genome in a ten year span, it is necessary for the automated sequencing devices to achieve a sequencing rate of three hundred million bases per year. At the same time, the sequence information obtained using these automated systems must be accurate, reliable, and efficient without requiring the involvement of highly skilled personnel to a high degree. In addition, the cost of operating and maintaining the automated sequencing devices must be minimized.

In the past, slab gel electrophoresis was used to sequence DNA. (See U.S. Pat. No. 4,811,218 and EPO 0533302A1, the disclosures of which are incorporated herein by reference). However, such techniques are prohibitively limited in the context of genomic sequencing efforts. Recently, capillary electrophoresis has emerged as a viable approach to genomic sequencing. In capillary electrophoresis the detectable products of sequencing reactions conducted on the nucleic acids to be sequenced are applied to small diameter capillary tubes containing a separating medium such as a soluble cellulose derivative or polyacrylamide. A high voltage is applied along the tubes, thereby causing the nucleic acids to migrate along the length of the capillary tubes. As in conventional sequencing techniques, the differential migration rates of nucleic acids of different lengths enables sequence determination. Nucleic acids migrating through the capillary tubes are detected upon reaching a detection region in the capillary tubes using such techniques as laser induced fluorescence.

While capillary electrophoresis permits high resolution of nucleic acids of different lengths and rapid sequence determination, several technical hurdles remain in the application of this technology to genomic sequencing efforts. One important limitation in existing methods is the difficulty in obtaining sequence information from a large number of capillaries simultaneously.

Huang et al. provided a device in which multiple capillaries are arrayed side by side as illustrated in FIG. 1, and are sequentially scanned by a laser and fluorescence is detected using a photomultiplier. (See Huang et al., Anal. Chem. 64:967–972 (1992), the disclosure of which is incorporated herein by reference). However, the effectiveness of the device of Huang is reduced as a result of lightscatter from the capillary walls and the interfaces between the separation medium and the capillaries. Furthermore, in the Huang device, the entire stage on which the capillaries are mounted is linearly translated back and forth underneath the light illumination and collection apparatus, resulting in stress on the capillaries and difficulties in precise position control.

Dovichi et al. provided a device in which multiple rows of capillaries terminate at different levels in a sheath flow cuvette. (See WO 94/29712, the disclosure of which is incorporated herein by reference). Sheath fluid draws individual sample streams through the cuvette. However, the device of Dovichi et al. requires a bubble removing system to ensure that bubbles do not form in the cuvette. To reduce background signal the Dovichi device requires the use of highly purified sheath fluid. In addition, in order to achieve the required sensitivity of signal detection, the Dovichi design requires placement of the laser very close to the termini of the capillaries. Finally, with the Dovichi system it is difficult to adjust the system after each use and to change the capillaries.

For the preceding reasons, there is a need for a detection system which achieves a high throughput while requiring little attention by highly trained personnel.

SUMMARY OF THE INVENTION

In one embodiment, the invention comprises an electrophoresis apparatus comprising a plurality of capillaries, wherein each of the plurality of capillaries intersects a plane, and wherein the plurality of capillaries is arranged to intersect the plane such that a curving contour is formed by the intersection points of each of the plurality of capillaries with the plane. Advantageously, such a plurality of capillaries may form a substantially cylindrical array.

Another aspect of the present invention includes an electrophoresis apparatus comprising a plurality of capillaries and a capillary guide. The capillary guide may form a substantially cylindrical shell having an inner surface and an outer surface and may include capillary inputs proximate to a first end and capillary outputs proximate to a second end. The capillaries may then be exposed along a portion of at least one of the inner surface and the outer surface of the capillary guide.

Methods of making electrophoresis apparatus are also provided. In one such embodiment of the invention, a method of making a capillary electrophoresis apparatus comprises the steps of arranging a plurality of capillaries in a substantially cylindrical array and mounting a light collecting lens adjacent to at least one of the plurality of capillaries.

Another aspect of the present invention comprises methods of performing electrophoresis. One such method comprises the steps of rotating an array of capillaries, illuminating capillaries in the rotating array and detecting light emitted by substances in said capillaries. An alternative method of performing electrophoresis comprises the steps of rotating an illuminator past an array of capillaries and detecting light emitted by substances in the capillaries.

Additional electrophoresis apparatus is also provided, including a grid for aligning capillaries with the wells in a microtiter plate. This grid advantageously comprises a body having apertures therein, the apertures being sized for receiving capillaries therein and configured such that the apertures align with the wells in the microtiter plate when the body is placed over the microtiter plate.

Another embodiment of the present invention is an apparatus comprising a first buffer chamber comprising a solid portion, at least one inlet channel in the solid portion, and at least one outlet channel in the solid portion, wherein the at least one inlet channel is in fluid communication with at least one inlet port, the at least one outlet channel is in fluid communication with at least one outlet port and the at least one inlet channel is in fluid communication with the at least one outlet channel. The apparatus also comprises a plurality of capillaries having first ends, second ends, and intermediate portions disposed between the first ends and the second ends, wherein the first ends extend into the first buffer chamber and are in fluid communication with the at least one inlet channel and the at least one outlet channel. In some aspects of this embodiment, the apparatus further comprising a second buffer chamber, wherein the second ends of the capillaries extend into the second buffer chamber. The apparatus may also further comprise an inlet receptacle in fluid communication with the inlet port and an outlet receptacle in fluid communication with the outlet port.

In other aspects of the above embodiment, the apparatus further comprises at least one cap positioned over the first ends of the capillaries, wherein the at least one inlet channel and the at least one outlet channel meet at the at least one cap. The apparatus may have a plurality of inlet channels radiating from a central inlet member and a plurality of outlet channels radiating from a central outlet member.

In other aspects of the above embodiment, the plurality of capillaries is arranged to intersect the plane such that a curving contour is formed by the intersection points of each of the plurality of capillaries with the plane. The curving contour may be substantially closed. The curving contour may form at least a portion of a circle. The capillaries may be arranged to intersect the plane at right angles thereto such that they form a substantially cylindrical array of capillaries.

In some aspects of the above embodiment, the apparatus further comprises an illuminator positioned inside of the substantially cylindrical array of capillaries. The illuminator may be rotatable such that the illuminator sequentially illuminates each capillary in the plurality of capillaries. The apparatus may further comprise a synchronization detector for obtaining data from the capillaries when an optical signal indicating that the capillaries are in focus is detected. The synchronization detector may be a photodetector.

In other aspects of the above embodiment, the apparatus further comprises an illuminator positioned outside of the substantially cylindrical array of capillaries. The substantially cylindrical array of capillaries may be rotatable such that each capillary in the plurality of capillaries is sequentially illuminated by the illuminator. The apparatus may further comprise a synchronization detector for obtaining data from the capillaries when an optical signal indicating that the capillaries are in focus is detected. The synchronization detector may comprises a photodetector.

In another aspect of the above embodiment, the apparatus further comprises a trigger for providing a signal indicative of the beginning of a new scanning cycle.

In another aspect of the above embodiment, the apparatus further comprises a light collector for detecting light emitted by substances within the capillaries, wherein the light collector comprises a spectral separator and at least one single line charge coupled device.

In some versions of the apparatus, the second buffer chamber comprises a grid.

The grid comprises a body having apertures therein, the apertures being sized for receiving capillaries therein and configured such that the apertures align with the wells in a microtiter plate when the body is placed over the microtiter plate. The grid also comprises a reservoir for holding electrophoresis medium. The reservoir for holding electrophoresis medium may comprise a microtiter plate and the grid further comprises a conducting plate positioned between the body and the microtiter plate, the conducting plate having leads thereon which extend into the wells of the microtiter plate.

Another embodiment of the present invention is a method of performing electrophoresis comprising obtaining an electrophoresis device comprising a first buffer chamber comprising a solid portion, at least one inlet channel in the solid portion, and at least one outlet channel in the solid portion, wherein the at least one inlet channel is in fluid communication with at least one inlet port, the at least one outlet channel is in fluid communication with at least one outlet port and the at least one inlet channel is in fluid communication with the at least one outlet channel and a plurality of capillaries having first ends, second ends, and intermediate portions disposed between the first ends and the second ends, wherein the first ends extend into the first buffer chamber and are in fluid communication with the at least one inlet channel and the at least one outlet channel. The method also comprises automatically directing an electrophoresis buffer/separation medium from the at least one inlet port into the first ends of the capillaries such that the capillaries become filled with the electrophoresis/separation medium. In addition, the method also comprises performing electrophoresis on samples introduced into the plurality of capillaries.

In some aspects of the above embodiment, the method further comprises washing the upper buffer chamber by automatically directing a wash solution into the at least one inlet port, from the at least one inlet port into the at least one inlet channel, and from the at least one inlet channel out the at least one outlet port. The method may further comprising opening the at least one inlet port and the at least one outlet port during the washing procedure.

The method may further comprise refilling the capillaries with the electrophoresis/separation medium by automatically directing an electrophoresis buffer/separation medium from the at least one inlet port into the first ends of the capillaries such that the capillaries become filled with the electrophoresis/separation medium. The method may further comprise opening the inlet port during the refilling procedure and closing the outlet port during the refilling procedure.

In some aspects of the above embodiment, the step of performing electrophoresis comprises placing samples into wells in a microtiter plate, positioning a grid having apertures therein over the microtiter plate such that the capillaries extend through the apertures and into the wells of the microtiter plate, and applying a voltage between the first buffer chamber and the second buffer chamber such that the samples move from the wells of the microtiter plate into the capillaries. The grid may further comprise a conducting plate having leads extending therefrom between the grid and the microtiter plate such that the leads extend into the microtiter plate. The method may further comprising filling the wells of the microtiter plate with electrophoresis buffer after the samples have entered the capillaries.

BRIEF DESCRIPTION OF THE DRAWINGS

FIG. 3 is a block diagram of a first embodiment of an electrophoresis apparatus in accordance with the present invention.

DETAILED DESCRIPTION OF THE PREFERRED EMBODIMENT

Preferred embodiments of the present invention will now be described with reference to the accompanying Figures, wherein like numerals refer to like elements throughout. The terminology used in the description presented herein is intended to be interpreted in its broadest reasonable manner, even though it is being utilized in conjunction with a detailed description of certain specific preferred embodiments of the present invention. This is further emphasized below with respect to some particular terms used herein. Any terminology intended to be interpreted by the reader in any restricted manner will be overtly and specifically defined as such in this specification.

Figure 2:
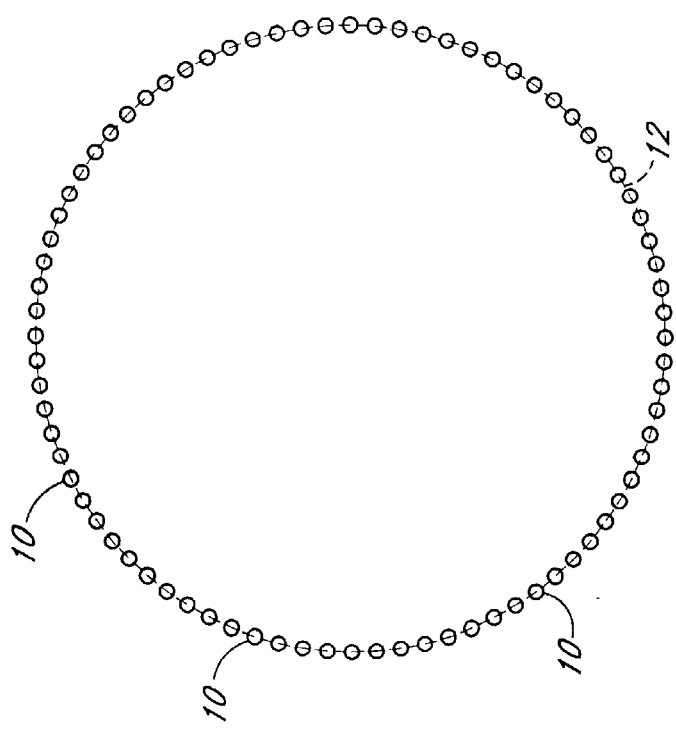
FIG. 2 is a cutaway end view of a cylindrical array of capillaries according to the present invention.
Figure 1:
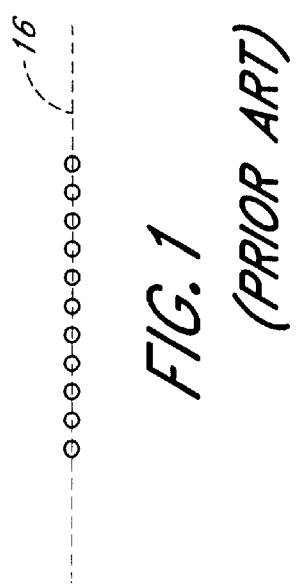
FIG. 1 is a cutaway end view of an open linear array of capillaries as provided by some prior art devices.

In one aspect of the present invention, an electrophoresis apparatus includes a novel arrangement of a plurality of capillaries. To illustrate, FIG. 2 shows a cutaway end view of a capillary arrangement according to one aspect of the present invention. As shown in this Figure, each of the capillaries 10 intersects a plane which in FIG. 2 would be transverse to the direction of capillary extension and parallel with the plane of the paper on which FIG. 2 is drawn. When the intersection points are connected, they form a curved contour 12 in the plane of intersection. In advantageous embodiments described in more detail below, the curved contour is substantially closed. In contrast, prior art multi-capillary electrophoresis machines, as shown in FIG. 1, only open linear contours 16 are created by linking their respective intersection points with a similarly defined plane. In one advantageous embodiment, the substantially closed contour which is formed is substantially circular. This specific arrangement is illustrated in FIG. 2. As will be explained below, a capillary arrangement which forms such a closed contour provides significant advantages over the linear arrangement of the prior art. Specifically, it is one advantage of such a configuration that various forms of rotating apparatus can be devised which allow improvements in speed and simplicity for high throughput electrophoresis screening. Two of these rotating configurations are described below with reference to FIGS. 3 and 4. In the FIG. 3 embodiment, an optical path for illumination and light collection rotates inside a capillary array. In the FIG. 4 embodiment, a capillary array rotates past a stationary optical path for illumination and light collection.

Referring now to FIG. 3, a first electrophoresis apparatus is illustrated which incorporates the capillary arrangement illustrated in FIG. 2. The illustrated electrophoresis apparatus includes a light source 30, which may advantageously comprise an approximately 50 milliwatt argon-ion laser commonly used for exciting fluorescence in various biological spectroscopy applications. The light source 30 transmits light 31 through first and second partially reflective mirrors designated 32 and 34 respectively. After passing through the mirrors 32, 34, the laser light is routed to an illuminator 36 which is positioned inside a substantially cylindrical capillary guide 20 (illustrated in cross section in FIG. 3) which supports a plurality of capillaries 10 in the arrangement of FIG. 2. In this embodiment, therefore, the illuminator 36 does not generate light, but only directs it to the capillaries 10. This is a preferred configuration, although a system having a light source 30 integral with the illuminator 36 may also be utilized.

Each capillary 10 extends into the guide 20 via a lower capillary input 22 on one end. Each capillary 10 exits the guide 20 through a capillary output 24 on the other end. In the FIG. 3 embodiment, the inputs 22 and outputs 24 comprise holes drilled through upper and lower portions of the guide 20. Along an inner surface 26 of the guide 20 the capillaries are exposed to the open inside region 28 of the guide 20. The capillaries may be held in place in grooves or indentations on the inner surface 26 of the guide with or without optical glue or other mechanical securement. Of course, the capillaries are connected on respective ends to buffer and sample material, as well as an electric potential for causing species migration through internal polymer. These aspects of some embodiments of the present invention are described in more detail below with reference to FIGS. 9–18.

The illuminator 36 directs the laser light 31 to the exposed portion of the capillaries on the inside of the guide 20. As will be explained in more detail below with reference to FIG. 5, in some advantageous embodiments the illuminator rotates inside the guide 20, so that each capillary 10 in the cylindrical array is sequentially exposed to the laser light 31. The illuminator further collects light emitted from substances within the capillary, from laser excited fluorescence, for example, with the same lens system used to route the laser light 31. A portion of this emitted light 38 is transmitted to a detector 40 by one of the partially reflective mirrors 34. The detector outputs data to a host computer system 42 to produce emission profiles for each capillary 10 in the array as a function of time. In some advantageous embodiments, the illuminator may rotate once around the array every 0.5 to 2 seconds, preferably approximately once per second, which will produce about 5 to 20 emission data points for a typical fluorescence band during, for example, DNA sequencing.

As is also seen in FIG. 3, the electrophoresis apparatus of the present invention may further comprise a synchronization detector 44. This detector may, for example, be a photodiode configured to be sensitive to light at the excitation frequency of the laser 30 which has been scattered by capillary surfaces and interfaces. The intensity of this scattered light will peak when the beam is centered directly over a capillary wall, and be minimal when the beam is between capillaries. This signal can be used to ensure the synchronization of data sampling and capillary illumination, and minimizes the amount of optics/capillary alignment which must be performed to collect data from hundreds or thousands of capillaries. In some embodiments, it is advantageous to include a larger space between the first capillary of an array and the last capillary of an array. The longer than usual period between signals from the synchronization detector thus produced can be detected and used to recognize the first capillary of the array. It will be appreciated by those of skill in the art that appropriate band-pass and/or band-stop filters may be used in the synchronization beam 45 and the collected emitted light beam 38.

Thus, the synchronization detector, such as a photodiode, may be used as a registration system to determine the position of the capillary from which data is being obtained and to determine the end of each scanning cycle. The photodetector detects the maximal optical signal produced when the capillary is in focus and converts the optical signal into an electrical pulse or signal. When the electrical pulse or signal is detected, data is collected from the capillary in focus.

In addition, a trigger which gives a different (e.g., long) electrical signal may be used to indicate that a new scanning cycle is beginning, allowing the position of the capillary from which data is being obtained to be registered. The trigger eliminates the need to use a complicated system for angle correlation and a step motor to ensure that the capillaries are aligned with the optical system at the moment when data is being collected. The trigger may produce the long electrical signal in any of a variety of manners familiar to those skilled in the art. For example, the trigger may produce a long optical signal which is converted into a long electrical signal. In one aspect of this embodiment, the trigger comprises a highly reflective material located between the last capillary in the array and the first capillary in the array. The reflective material may have a width sufficient to generate a long optical signal when the illuminator is illuminating a region between the last capillary in the array and the first capillary in the array. It will be appreciated that the trigger may be used in embodiments in which the illuminator rotates as well as in embodiments in which the array rotates.

Figure 9:
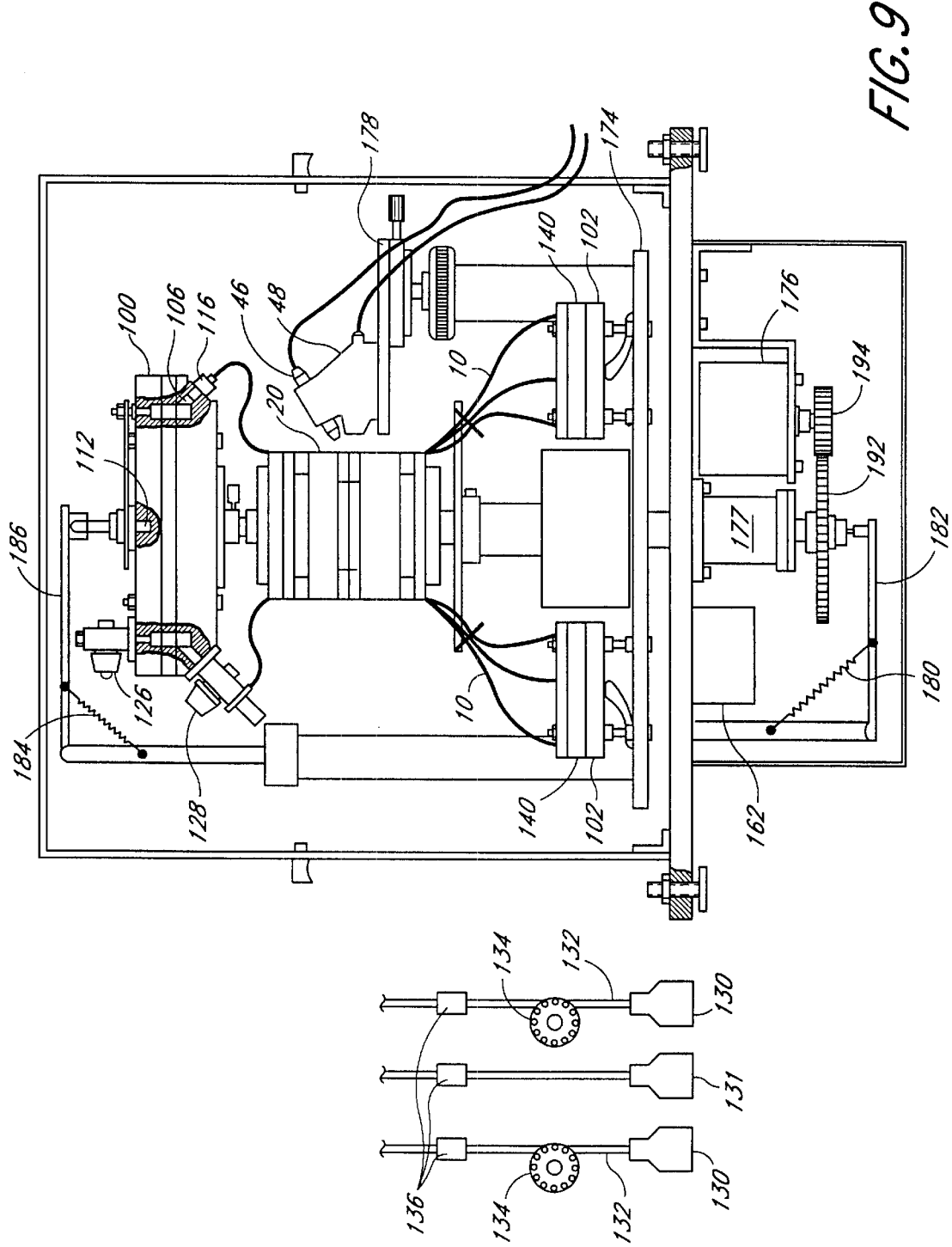
FIG. 9 is a cutaway view of a stationary optical path embodiment of the electrophoresis apparatus of the present invention.

Preferably, the trigger generates a long electrical signal directly. For example, the trigger may generate a long electrical signal when the motor driving the rotation of the array or the illuminator reaches a position in which the illuminator is between the last capillary in the array and the first capillary in the array. For example, as best illustrated in FIG. 9, the electrical signal may be generated when a particular point on gear 194 contacts gear 192. The point on gear 194 is selected such that the point contacts gear 192 when the motor is in a position where the illuminator is illuminating a region between the last capillary in the array and the first capillary in the array. In some embodiments, electrical signal may be generated using an electrical circuit, such as an integrated circuit, which generates an electrical signal when the illuminator is illuminating a region between the last capillary in the array and the first capillary in the array. It will be appreciated that the trigger may be used in embodiments in which the illuminator rotates as well as in embodiments in which the array rotates.

Alternatively, any appropriate structure or software may be utilized to ascertain the position of the illuminator vis a vis the capillaries in the array. For example, a mechanical or optical switch can be opened or closed at a particular position, e.g., when the illuminator illuminates the first or last capillary, or in between such illumination. Similarly, where a fixed number of capillaries are used, a software routine can be used to count the number of capillaries illuminated and to thus ascertain when a complete revolution has been made. A target having a different spectral signature than a capillary can be used between a pair of capillaries as a position indicator, as can a plurality of targets that are the same or different between multiple pairs or even all of the capillaries. Similarly, use of a stepper motor or gearing in combination with optical detection, can also be used to ascertain the spatial relationship of the illuminator and the capillaries.

Figure 4:
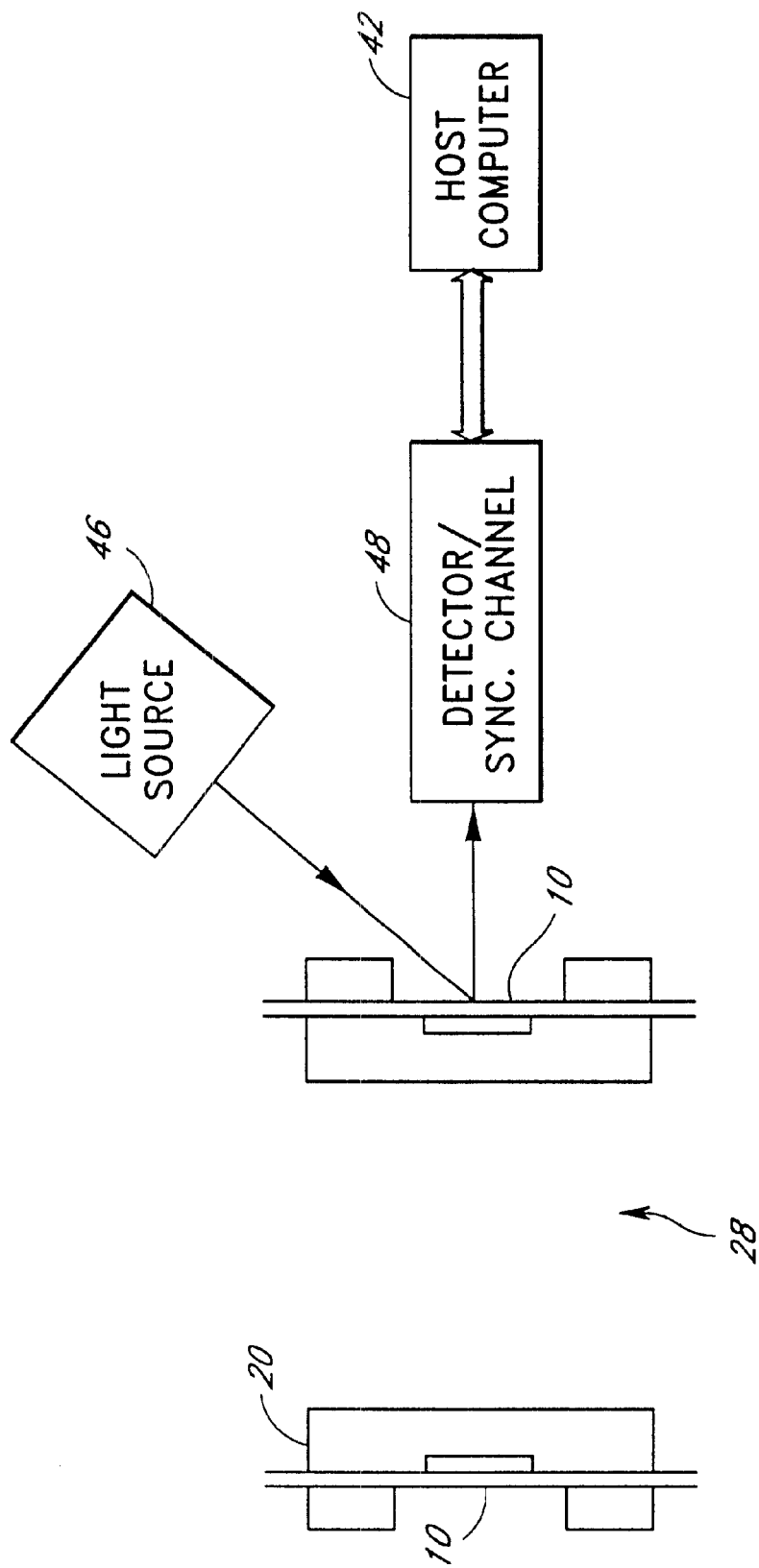
FIG. 4 is a block diagram of a second embodiment of an electrophoresis apparatus in accordance with the present invention.

An additional embodiment having a stationary optical path and a rotating capillary guide 20 is illustrated in FIG. 4. In this embodiment, the inside region 28 of the guide 20 contains no illuminator, and the capillaries 10 are secured to the outer surface of the guide 20 rather than the inner surface. A light source 46, of a nature similar to that described above with regard to FIG. 3, is provided outside the guide 20 so as to illuminate the capillaries 10 on the outer surface of the guide. In addition, a detector 48, coupled to a host computer 42 are also provided outside the guide 20. In this, embodiment, as will also be described below with reference to FIG. 7, the synchronization channel is provided as part of the detector assembly 48.

As described above with respect to the embodiment of FIG. 3, in the embodiment of FIG. 4, the synchronization detector, such as a photodiode, may be used as a registration system to determine the position of the capillary from which data is being obtained and to determine the end of each scanning cycle. The photodetector detects the maximal optical signal produced when the capillary is in focus and converts the optical signal into an electrical pulse. When the electrical pulse is detected, data is collected from the capillary in focus.

Figure 7:
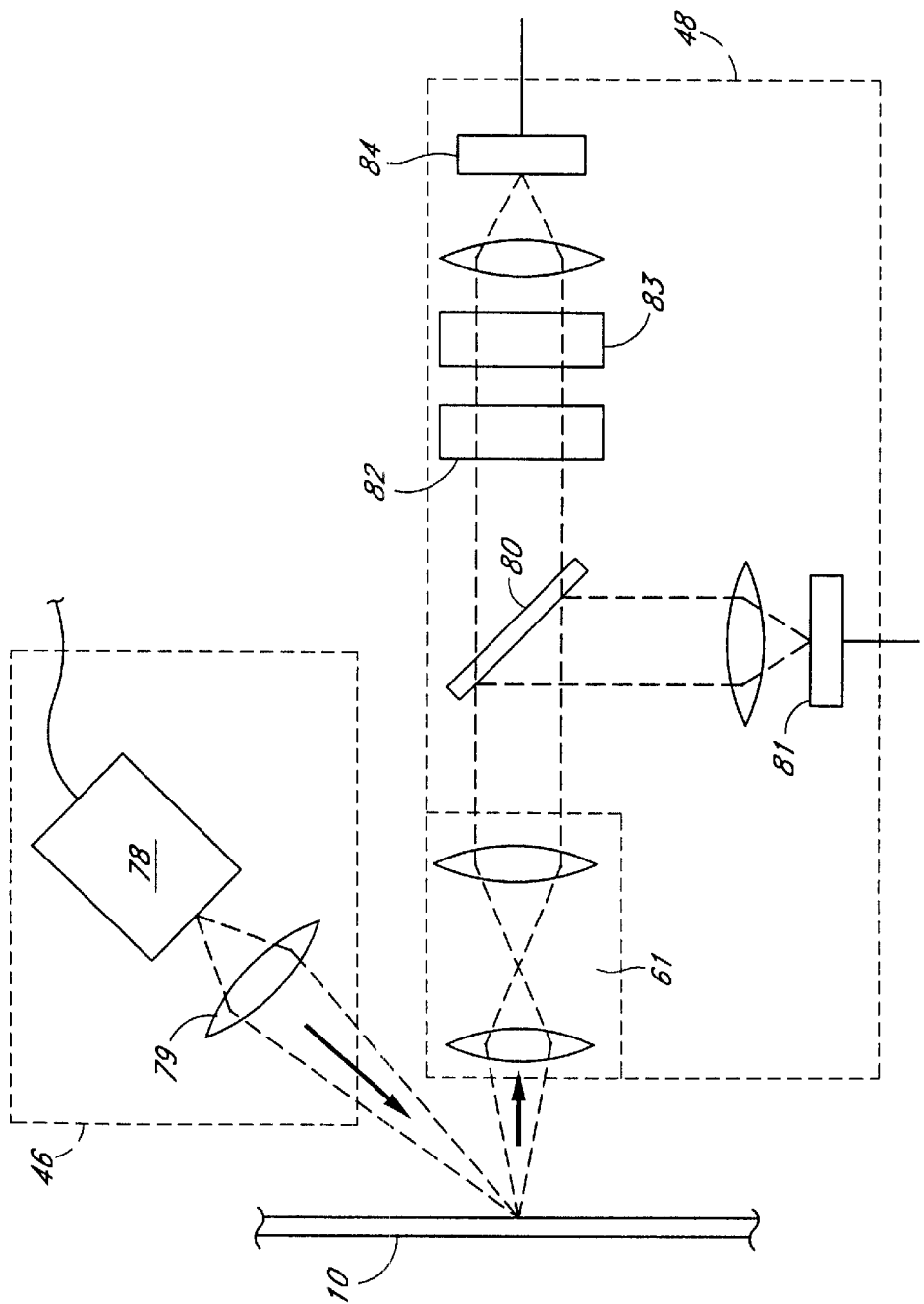
FIG. 7 is a detailed view of the detector/synchronization channel of FIG. 4.

In the embodiment of FIG. 4, the guide 20 and attached capillary array rotate, while the light source and collection apparatus remain stationary. In this embodiment, the capillary array may rotate approximately 0.5 to 2 times per second, preferably approximately 1 revolution per second. Although the configuration of FIG. 4 requires moving capillaries which are not required in the FIG. 3 embodiment, the light path remains stationary, thereby simplifying the optics of the system. It will be appreciated that the optics used in this embodiment may comprise either a confocal system, such as that illustrated in FIG. 5, or a non-confocal system as illustrated in FIG. 7. In particular, accurate focusing of the light beam is easier with this embodiment, because no precise alignment of the beam with the central portion of a rotating mirror is needed.

The advantages to the curved contour capillary array configuration over the linear array may now be appreciated, and can be seen to increase substantially with increases in the number of capillaries in a given array. Because the rotation rate will remain constant regardless of the number of capillaries in the array, the mechanical problems associated with scanning truly large numbers of capillaries are greatly reduced. Furthermore, the fact that the array of capillaries defines a closed contour (as described above with reference to FIG. 2) allows the scanner to be adjacent to the first capillary immediately following a scan of the last capillary. This is not possible with the open contour linear array, where a return to the opposite side of the array must be made after each pass. This results in an overall decrease in the average relative speed over a given distance between the capillaries and the light beam optics of about 50% as compared to the open contour linear capillary array.

For example, with one millimeter between the center of each capillary 10, a 1000 capillary electrophoresis device according to the present invention as illustrated in FIG. 4 may include an approximately 1 Hz rotating capillary guide which is approximately 37 cm diameter cylindrical capillary array. For a similar linear array, the array width would be one meter, and the linear speed of the beam optics relative to the capillaries would need to average at least 2 meters per second. This linear scanning motion would further include large accelerations as it changed direction at either end of the array. As the number of desired capillaries increases above this example 1000 capillary array, the relative ease of upward scaling of the cylindrical array relative to the linear array becomes even more pronounced.

Figure 5:
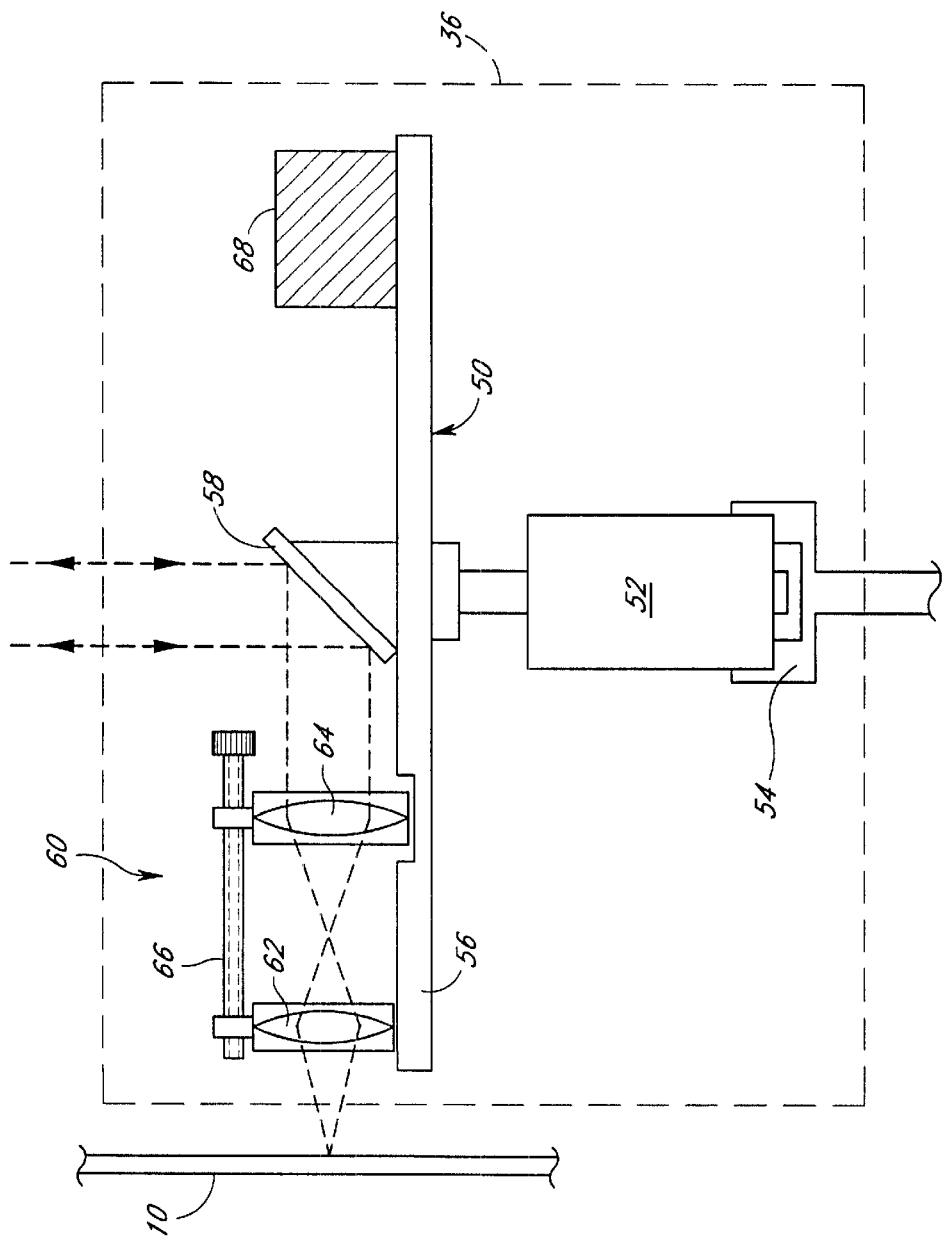
FIG. 5 is a detailed view of the illuminator of FIG. 3.

Referring now to FIG. 5, a detailed illustration of one advantageous embodiment of the illuminator 36 of FIG. 3 is provided. The illuminator 36 may comprise a platform 50 mounted on the shaft of a motor 52 which is held inside the capillary guide 20 by a support arm 54 which extends out one end of the capillary guide 20. The platform has a length so that at least one end 56 extends almost to the inner surface 26 of the capillary guide 20. The platform 50 provides a mounting surface for a centrally located mirror 58 which is angled at approximately 45 degrees from the horizontal.

At one end 56 of the platform 50 is a conventional compound microscope 60 which may take any one of many forms known in the art. In FIG. 5, the microscope is illustrated as comprising an objective lens 62, an eyepiece 64, and a focus adjustment screw 66. The microscope 60 focuses the laser light onto a region inside an adjacent capillary 10, and also collects light emitted by substances within the capillary 10 in a manner well known in the art. The platform may further have mounted thereon a counterweight 68, which can be adjusted in weight and position to provide rotational stability to the platform 50.

Figure 6:
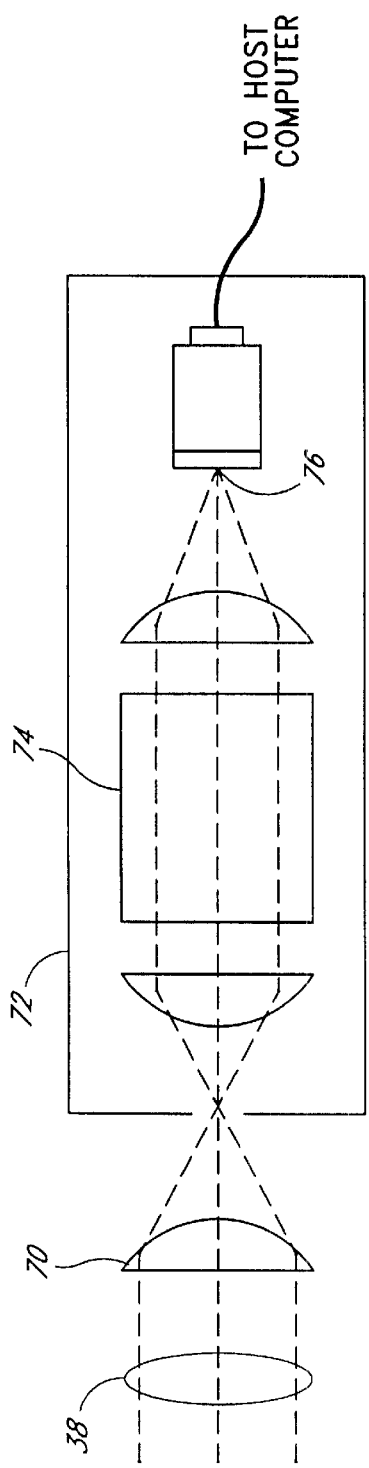
FIG. 6 is a detailed view of the detector of FIG. 3.

FIG. 6 is a more detailed illustration of the detector 40 of FIG. 3. The detector comprises a lens 70 which focuses the emitted light beam 38 through a small opening in a substantially light tight enclosure 72. Inside the enclosure is a spectral separator 74, which transmits light of different wavelengths emitted by the illuminated region of the capillary onto different locations on a linear, single line charge coupled device (CCD) 76. Spectral separators including prisms or diffraction gratings which are suitable for use with the present invention are well known to those of ordinary skill in the art. Thus, for DNA sequencing using a different fluorescent dye for each base, the CCD can be broken up into regions corresponding to the approximate emission wavelength of each dye.

It can be appreciated that the configuration of the apparatus for illuminating and detecting fluorescence is somewhat different for the rotating capillary array of FIG. 4. One advantageous embodiment of this apparatus is illustrated in FIG. 7. As shown in FIG. 7, the light source 46 comprises a source of laser light 78 analogous to that described above. In this embodiment, the laser light may advantageously be routed to the capillary array through an optical fiber. The light source 46 also comprises an appropriate focusing objective lens 79. The detector/synchronization channel 48 includes a microscope 61 analogous to the microscope 60 of the illuminator 36 of FIGS. 3 and 5. The angle between the illuminating light beam and the axis of the light collecting objective is advantageously approximately 45 degrees.

The synchronization channel is created by a partially reflective mirror 80 (an unsilvered glass plate has been found suitable) which directs a small amount of the collected light to a photodiode 81, and operates in a manner analogous to that described above with reference to FIG. 3. The detector 48 additionally includes a rejection filter 82 after the mirror 80 for filtering out light at the fluorescence excitation frequency. A spectral separator 83 and CCD array 84 as described above with reference to FIG. 6 are further provided.

Figure 8:
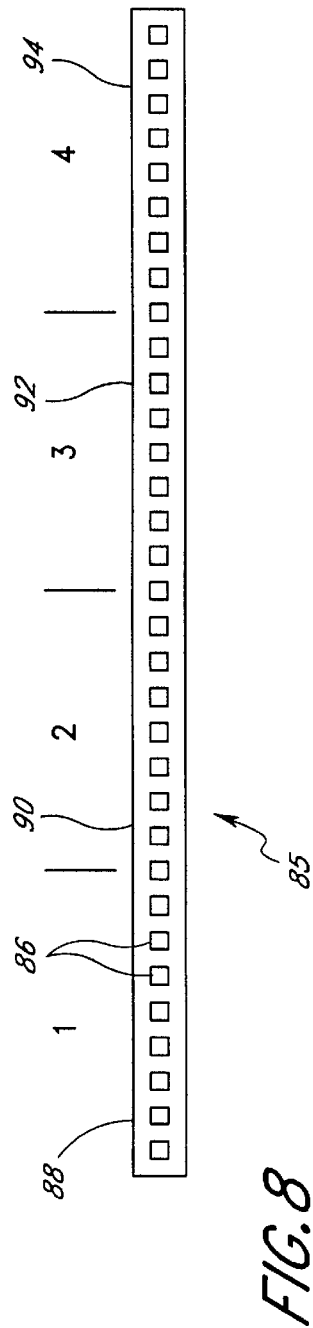
FIG. 8 is an front view of the single line charge coupled device of FIG. 6 and FIG. 7.

A more detailed view of the single line charge coupled device 85 is provided in FIG. 8. As shown in this Figure, the device 85 comprises a linear array of pixels 86. Captured charges which result from incident photons on each pixel are periodically read out. It will be appreciated that the pixels of FIG. 8 are representative only, and that their number and size may vary. This array is positioned relative to the spectral separator 74, 83 (FIGS. 6 and 7) such that light from different fluorescent dyes will illuminate different portions of the linear CCD array. In a four dye DNA sequencing scheme, for example, the array can be segmented into four adjacent regions 88, 90, 92, 94, each chosen to span the peak emission wavelength of one of the four dyes being used. With this system a single CCD array can be used to distinguish multiple dye emissions of different wavelengths without the use of filters.

In prior art capillary electrophoresis apparatus, the typical light detector has been a photomultiplier tube. One reason these devices have been preferred over CCD detectors is that the output is a real-time continuous readout of incident light intensity. In contrast, a CCD element must collect charge for a given period of time under illumination, and this must be followed by a pixel read operation, during which time the collected charge is read out, but the incident light intensity is not being measured. The time taken for this data read operation may limit the rate at which capillaries can be scanned by any one individual CCD pixel. In some embodiments of the present invention, the readout is performed when the illuminating beam is between capillaries. It has been found suitable to leave a space between capillaries of approximately one capillary in width for the read operation. Because the time between capillary illuminations is used for reading out the intensity data, impact on scanning speed is reduced.

The host computer 42 receives this intensity data from the CCD array and interprets the detected light to deliver information to the user regarding the substances which are passed through the capillaries. In one specific example, DNA may be sequenced with a four spectral channel method, where each terminating base is coupled to a dye which fluoresces at a different wavelength. This technique is also described in more detail below, and is currently performed in various electrophoresis protocols. In this example, the host computer 42 may create four separate data files for each capillary. Each file comprises a series of intensity measurements made at approximately one second intervals, with each measurement being a weighted sum of the measured intensities for pixels in a respective one of the four segments of the array. These data sets can be processed in a variety of ways. Spectral cross talk can be eliminated by correlating measurements from adjacent capillaries, and time or frequency domain low pass filtering may be performed. Mobility shift compensation can also be performed prior to peak detection and base identification. Preferably, this process results in a printed 4-letter format base sequence for the DNA sample tested through a given capillary.

Figure 10:
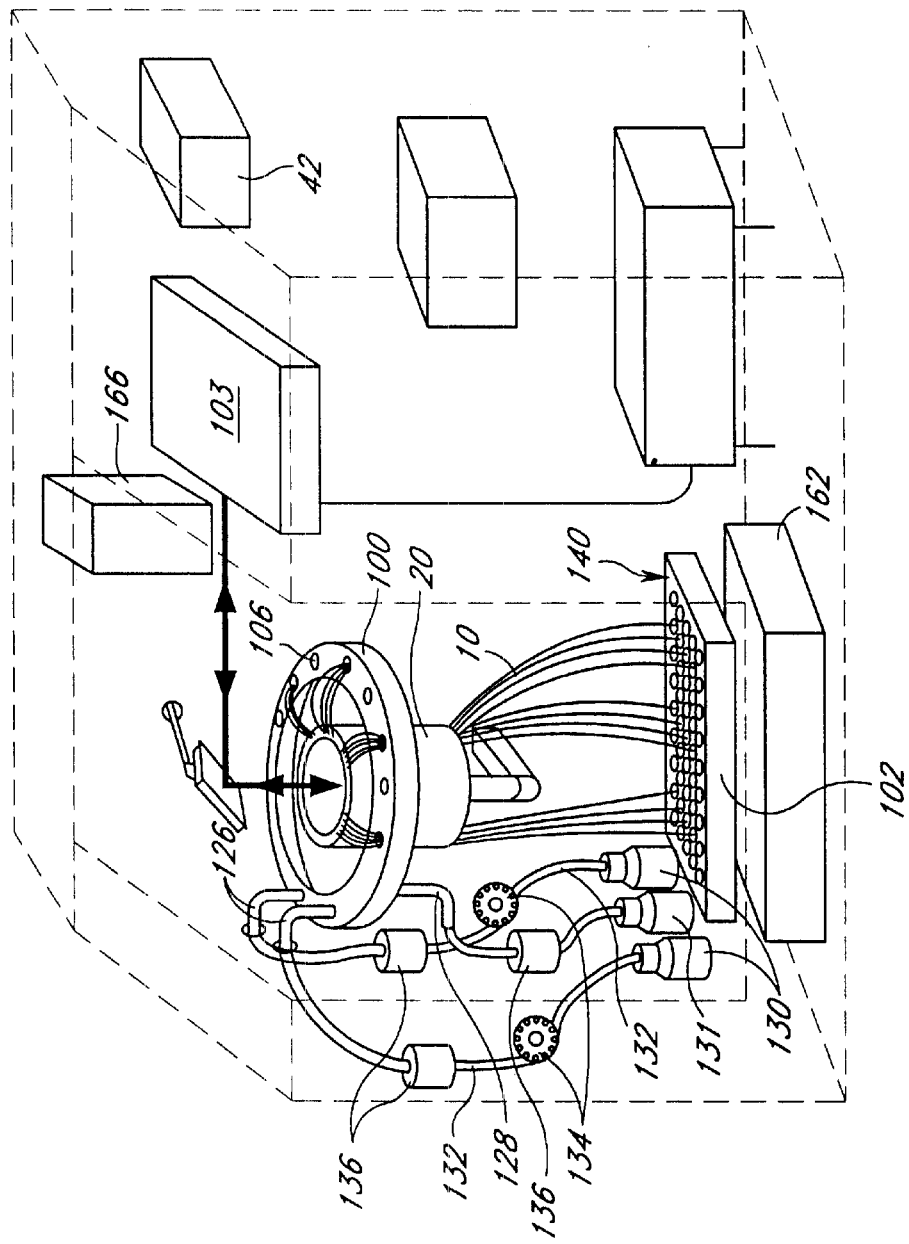
FIG. 10 is a cutaway view of a rotating optical path embodiment of the electrophoresis apparatus of the present invention.

In addition to the detection system described above, the electrophoresis apparatus comprises an electrophoresis portion illustrated in detail in FIGS. 9 and 10. This electrophoresis portion comprises an upper buffer chamber, a lower buffer chamber, a plurality of capillaries extending between the upper buffer chamber and the lower buffer chamber, and a voltage source 162 connected to the upper buffer chamber and the lower buffer chamber. In some embodiments, the electrophoresis portion may further comprise a capillary guide which supports the portions of the capillaries disposed between the upper buffer chamber and the lower buffer chamber. In addition, in some embodiments, the electrophoresis portion of the electrophoresis apparatus may further comprise a filling/refilling system for filling and refilling the capillaries and upper buffer chamber with buffer/separation medium without detaching the capillaries from the device. In some embodiments, the electrophoresis portion is thermoisolated from the remainder of the system such that the temperature at which electrophoresis is performed can be regulated and maintained.

Two embodiments of the present invention are illustrated in FIGS. 9 and 10. However, it will be appreciated that the physical arrangement of the components of the present electrophoresis system may be varied from those shown in FIGS. 9 and 10 without affecting the operation of the device. Accordingly, those of skill in the art will appreciate that such variations fall within the scope of the present invention.

As discussed above in conjunction with FIG. 4, the present invention includes an embodiment wherein the optical path remains stationary while the capillary guide rotates. On such embodiment, illustrated in FIG. 9, will be referred to herein as the "stationary optical path embodiment." In another embodiment, discussed above with reference to FIG. 3, the optical path rotates while the capillary guide remains stationary. One such embodiment, illustrated in FIG. 10, will be referred to herein as the "rotating optical path embodiment." In FIG. 10, the illuminator is inside the capillary guide 20, and is accordingly not shown in this Figure.

As shown in FIGS. 9 and 10, the upper buffer chamber 100 is disposed above one or more lower buffer chambers 102. A plurality of capillaries 10 are disposed between the upper buffer chamber 100 and the lower buffer chambers 102. As shown in FIGS. 9 and 10, a capillary guide 20 may be disposed between the upper buffer chamber 100 and the lower buffer chamber 102. The capillary guide 20 provides support for the portions of the capillaries 10 disposed between the upper buffer chamber 100 and the lower buffer chambers 102. In addition, the capillary guide 20 fixes the capillaries 10 in a closed contour configuration as described above. Preferably, the capillary guide 20 is a cylindrical tube with a circumference smaller than the circumference of the upper buffer chamber 100. The capillaries 10 are secured to the capillary guide by optical glue, spring rings, or other securing devices known to those skilled in the art.

In the rotating optical path embodiment of FIG. 10, a portion of each of the capillaries 10 passes through the interior of the capillary guide 20 as illustrated in cross section in FIG. 3. In the stationary optical path embodiment, at least a portion of each of the capillaries is disposed on the exterior of the capillary guide 20.

In the stationary optical path embodiment of FIG. 9, the upper buffer chamber 100, capillary guide 20, capillaries 10, and lower buffer chambers 102 are mounted on a platform 174. The platform 174 is driven by a motor 176 which is coupled to a drive shaft/gear box 177. When the motor 176 is activated, the platform 174 rotates. As discussed above, the motor may rotate the platform at a rate of about 0.5 to 2 revolutions per minute. Preferably, the motor rotates the platform at a rate of about 1 revolution per minute.

As the platform 174 rotates, the capillaries 10 on the exterior of the capillary guide 20 sequentially pass in front of the illuminator 46 which is mounted on a fixed platform 178. As each capillary passes before the illuminator 46, the capillary is exposed to the laser light, and the light emitted from the sample passing through the illuminated portion of the capillary is detected.

In the rotating optical path embodiment of FIG. 10, the light source 30, synchronization channel 44, and detector 40 of FIG. 3 are all provided inside a single light tight enclosure 103. In this embodiment, the capillary guide 20 is fixed in place and the illuminator 36 rotates inside the central cavity of the capillary guide. The capillaries 10 are sequentially exposed to laser light by the rotating illuminator 36 positioned inside the central cavity of the capillary guide 20.

As illustrated in FIGS. 9 and 10, an electrical power source 162 is electrically connected to the upper buffer chamber 100 and the lower buffer chambers 102. Those skilled in the art will appreciate that the upper buffer chamber 100 and the lower buffer chamber 102 can be electrically connected to the power source 162 in a variety of ways. For example, in the stationary optical path embodiment of FIG. 9, the electrical power source 162 may be electrically connected to the lower buffer chambers 102 via contacts 180 and 182 beneath the rotating platform 174. One end of contact 182 may be electrically connected to conductors inside the lower buffer chambers 102.

In the rotating optical path embodiment of FIG. 10, the lower buffer chambers 102 may be directly connected to the electrical power source 162.

Figure 11:
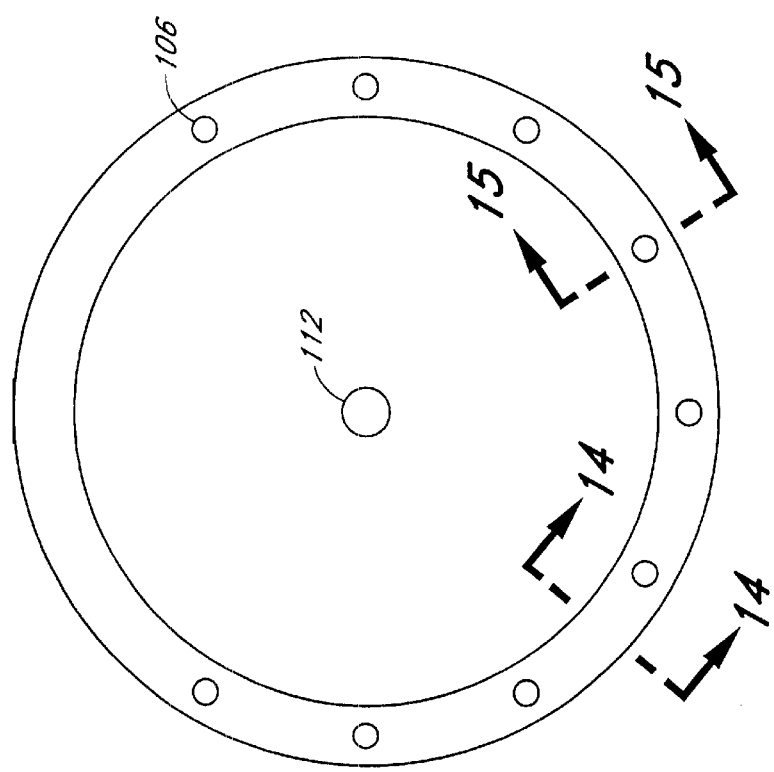
FIG. 11 depicts the bottom of the upper buffer chamber of the stationary optical path embodiment of FIG. 9.
Figure 13:
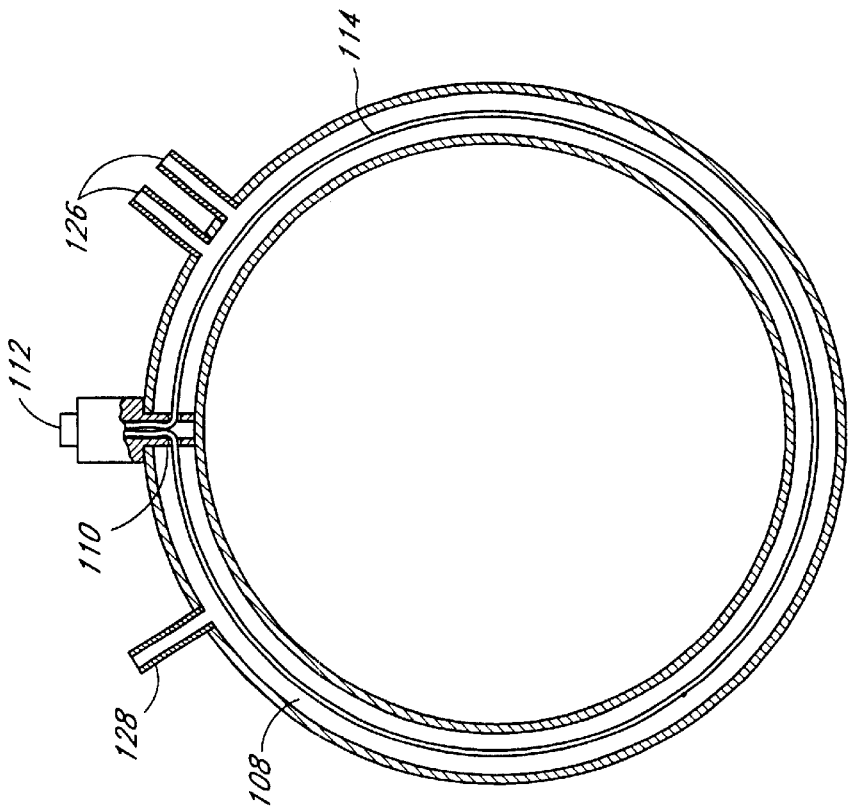
FIG. 13 is a cross section of the upper buffer chamber of FIG. 12.
Figure 12:
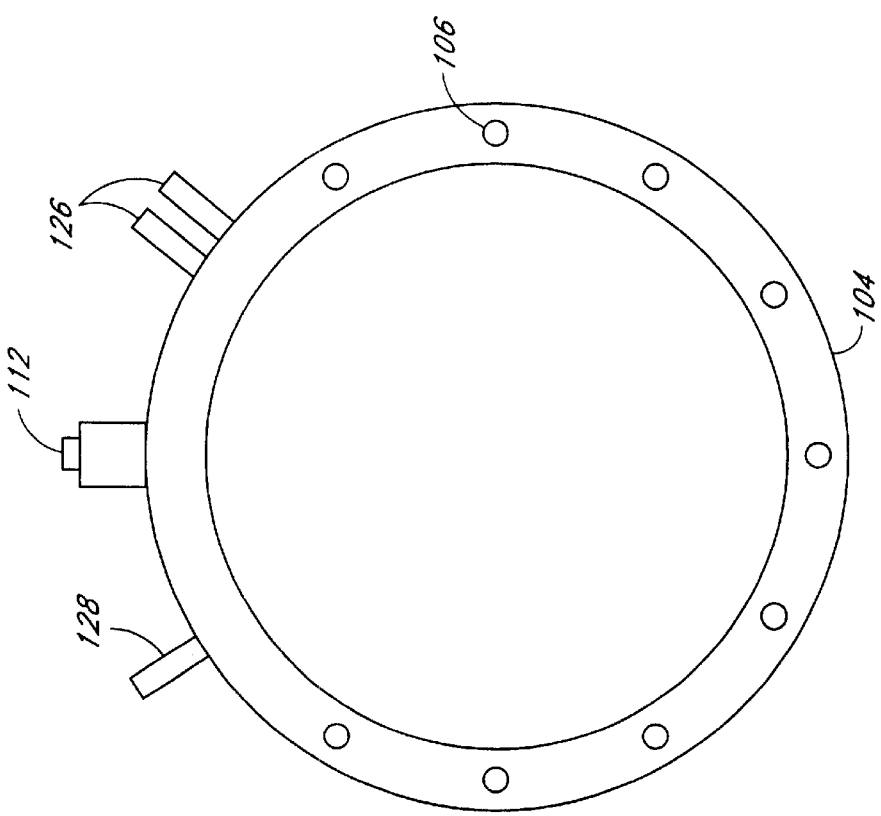
FIG. 12 is a top view of the upper buffer chamber of the rotating optical path embodiment of FIG. 10.

The structure of the upper buffer chamber 100 is shown in more detail in FIGS. 11, 12, and 13. The upper buffer chamber 100 comprises a housing 104 having one or more apertures 106 therein for receiving the upper portions of the capillaries 10.

FIG. 11 depicts the bottom of the upper buffer chamber 100 of the stationary optical path embodiment of FIG. 9. As illustrated in FIG. 11, in this embodiment, the apertures 106 may be located on the lower surface of the upper buffer chamber 100. A spindle 112 runs through the center of the upper buffer chamber 100 to electrically connect the upper buffer chamber 100 to a voltage source 162 through contacts 184 and 186. The spindle 112 is mechanically connected to the motor 176 through gears 192 and 194.

FIG. 12 is a top view of the upper buffer chamber of the rotating optical path embodiment of FIG. 10. FIG. 13 is a cross section of the upper buffer chamber of FIG. 12. As illustrated in FIGS. 12 and 13, in the rotating optical path embodiment of FIG. 10, the apertures 106 may be located on the upper surface of the upper buffer chamber 100.

The upper buffer chamber 100 may have a variety of configurations which array the capillaries 10 in a substantially closed contour. Preferably, the upper buffer chamber 100 is annular in shape. In some embodiments, the interior of the apertures 106 may be threaded to receive an adapter for securing the capillaries 10 to the upper buffer chamber 100 as described below.

Figure 15:
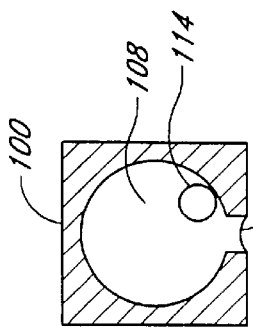
FIG. 15 is a cross section of the upper buffer chamber of FIG. 11 taken along line 15—15.
Figure 14:
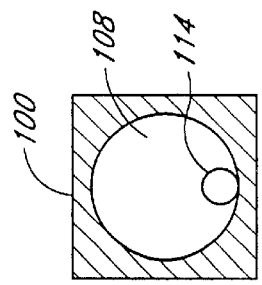
FIG. 14 is a cross section of the upper buffer chamber of FIG. 11 taken along line 14—14.

As shown in FIGS. 13, 14, and 15 the interior of the upper buffer chamber 100 has a channel 108 therethrough for receiving the electrophoresis buffer/separation medium. The channel 108 runs throughout the circumference of the upper buffer chamber 100 but may be interrupted by a partition 110 (illustrated in FIG. 13) in those embodiments equipped with a filling/refilling system as described below. The partition 110 permits the flow of electrophoresis buffer/separation medium to be directed along a desired path during filling or refilling. As shown in the cross section of FIG. 15, the channel 108 in the upper buffer chamber is in fluid communication with the apertures 106 therein.

A connector 112 for connecting the upper buffer chamber 100 to a voltage source 162 is located on the exterior of the upper buffer chamber 100. In the stationary optical path embodiment, the connector 112 may be a spindle which extends from the motor through the upper buffer chamber 100 as illustrated in FIG. 11.

In the rotating optical path embodiment, the connector 112 may be on the side of the upper buffer chamber 100 as illustrated in FIGS. 12 and 13.

As illustrated in FIGS. 13, 14, and 15 an electrical conductor 114 is positioned on the lower surface of the channel 108 and runs along the entire circumference of the upper chamber 100. As shown in FIG. 13, in some embodiments having a partition 110 in the channel 108, such as the rotating optical path embodiment of FIG. 10, the electrical conductor 114 passes through the partition 110 and is secured to the connector 112, thereby allowing the potential difference from the voltage source 162 attached to the connector to be applied across the buffer in the upper chamber 100. Alternatively, in some embodiments having a partition 110 in the channel 108, such as the stationary optical path embodiment of FIG. 9, the potential difference from the voltage source 162 may be applied through the spindle 112. In those embodiments which lack the partition 110, the electrical conductor is secured to the connector or spindle 112 on the interior surface of the upper buffer chamber 100.

As shown in FIGS. 9 and 10, bundles of capillaries 10 pass through the apertures 106 in the upper buffer chamber 100. The capillaries 10 may be any of the capillaries conventionally used for capillary electrophoresis, such as the fused silica capillary tubes available from Polymicro, Phoenix, Ariz. having inner diameters of between 50 $\mu$m to 100 $\mu$m or more, preferably 75 $\mu$m. The number of bundles of capillaries 10 entering the upper buffer chamber 100 may vary depending on the number of samples which are to be evaluated in each run. Preferably, there are a plurality of bundles of capillaries 10 attached to the upper buffer chamber 100. The number of capillaries 10 in each bundle may vary depending on the number of samples which are to be evaluated in each run. Preferably, there are at least 50 capillaries in each bundle.

Figure 16:
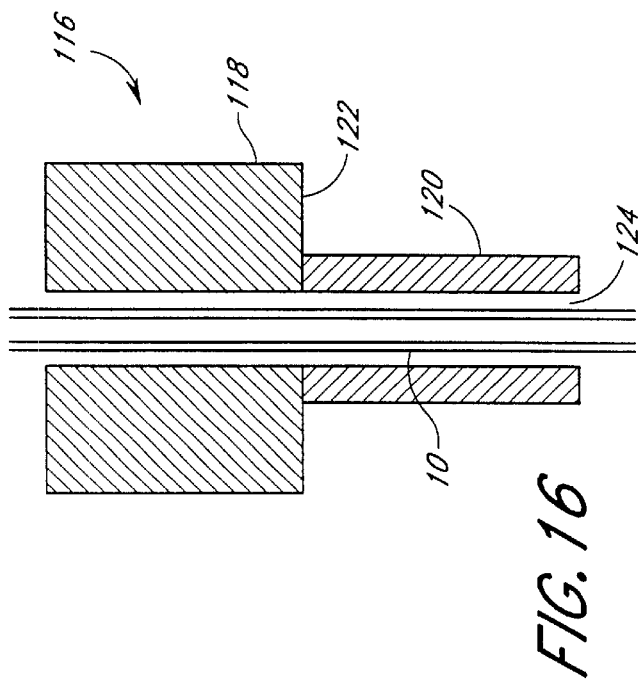
FIG. 16 is a cross section of an adapter for connecting the capillaries to the upper buffer chamber.

The bundles of capillaries 10 may be connected to the upper buffer chamber 100 via an adapter 116 such as the adapter illustrated in FIG. 16. The adapter 116 of FIG. 16 comprises a stopper section 118 and an insertion section 120. The stopper section 118 is wider than the insertion section 120, thereby forming a shoulder 122 at the junction between the stopper section 118 and the insertion section 120. The shoulder 122 prevents the stopper section 118 of the adapter 116 from being inserted into the upper buffer chamber 100. A channel 124 runs through the stopper section 118 and the insertion section 120. The exterior of the insertion section 120 may be threaded to permit it to be screwed into threads in the apertures 106 in the upper buffer chamber 100, thereby securing the adapter 116 to the upper buffer chamber 100. A bundle of capillaries 10 passes through the channel 124 in the adapter 116 such that when the insertion section 120 of the adapter 116 is inserted into one of the apertures 106 in the upper buffer chamber 100, the ends of the capillaries 10 will contact the buffer solution in the channel 108 in the upper buffer chamber 100. The capillaries 10 may be secured to the adapter 116 using optical glue or, alternatively, the interior of the adapter may have grooves or channels therein which secure the capillaries in place.

The embodiments depicted in FIGS. 9 and 10 may include a filling/refilling system for filling or refilling the capillaries 10 and upper buffer chamber 100 with electrophoresis buffer/separation medium without detaching the capillaries 10 from the device. As illustrated in FIGS. 9 and 10, in those embodiments equipped with a filling/refilling system, the upper buffer chamber 100 has at least one inlet port 126 for introducing buffer/separation medium and at least one outlet port 128 for removing buffer/separation medium. In some embodiments, there may be a single port which functions as both an inlet port and an outlet port. Alternatively, the inlet port and the outlet port may be distinct. Furthermore, in some embodiments there may be a plurality of inlet ports and outlet ports. The inlet ports 126 and outlet ports 128 are connected to the apertures 106 in the upper buffer chamber 100 such that the inlet ports 126 and outlet ports 128 are in fluid communication with the channel 108 in the upper buffer chamber 100.

As described in more detail below, when it is desired to fill or refill the capillary tubes 10 and upper buffer chamber 100 with buffer/separation medium, the buffer/separation medium is introduced via the inlet ports 126. Before refilling the capillary tubes 10, the buffer/separation medium used in the previous electrophoresis run may be flushed from the upper buffer chamber 100 and capillary tubes 10 by introducing buffer/separation medium or a rinsing solution through the inlet ports 126 and draining the solution through the outlet ports 128.

In the rotating optical path embodiment of FIG. 10, the inlet ports are in fluid communication with inlet receptacles containing buffer/separation medium via tubing 132 disposed between the inlet receptacles 130 and the inlet ports. The outlet ports 128 are also in fluid communication with outlet receptacles 131 for receiving fluid being drained from the upper buffer chamber 100 via tubing 132 disposed between the outlet receptacles 131 and the outlet ports 128. In the rotating optical path embodiment of FIG. 10, the inlet ports 126 may be connected to the tubing 132 from the inlet receptacles 130 at all times, including during the operation of the device. Alternatively, if desired, the inlet ports 126 may be connected to the tubing 132 from the inlet receptacles 130 only during filling or refilling of the upper buffer chamber 100. Similarly, in this embodiment, the outlet ports 128 may be connected to the tubing from the outlet receptacles 131 at all times, including during the operation of the device. Alternatively, if desired, the outlet ports 128 may be connected to the tubing from the outlet receptacles 131 only during filling/refilling of the upper buffer chamber 100.

In the stationary optical path embodiment of FIG. 9, the inlet ports 126 are not connected to the tubing from the inlet receptacles 130 during the operation of the device. Instead, the inlet ports 126 are connected to the tubing from the inlet receptacles 130 during filling/refilling of the upper buffer chamber 100 while the platform 174 is not rotating. Similarly, in this embodiment, the outlet ports 128 are not connected to the tubing from the outlet receptacles 131 during the operation of the device. Instead, the outlet ports 128 are connected to the tubing from the outlet receptacles 131 during filling/refilling of the upper buffer chamber 100 while the platform 174 is not rotating.

As illustrated in FIGS. 9 and 10, high pressure pumps 134 may be disposed between each inlet port 126 and inlet receptacle 130. The high pressure pumps are preferably capable of generating pressures up to 70 atmospheres, more preferably between about 50 and about 60 atmospheres. Electromagnetic valves 136 are disposed between the inlet ports 126 and the inlet receptacles 130. Electromagnetic valves 136 are also disposed between the outlet ports 128 and the outlet receptacles 131. When the electromagnetic valves 136 are in open position, fluid in the inlet receptacles 130 which are in fluid communication with the inlet ports 126 can be pumped by the high pressure pumps 134 from the inlet receptacles 130 into the channel 108 in the upper buffer chamber 100 and into the capillaries 10. When the electromagnetic valve 136 connected to the outlet port 128 is open, fluid can drain from the outlet port 128 into the outlet receptacle 131 connected to the outlet port 128.

When it is desired to fill the upper buffer chamber 100 and capillaries 10 with fluid, the electromagnetic valves 136 connected to the inlet ports 126 (and/or the inlet ports themselves) are opened and the high pressure pumps 134 are activated. Fluid is pumped from the receptacles 130 connected to the inlet ports 126 into the channel 108 in the upper buffer chamber 100 and into the capillary tubes 10. If it is desired to empty or flush electrophoresis buffer/separation medium already in the channel 108 in the upper buffer chamber 100 and capillaries 10, the electromagnetic valves 136 connected to the inlet ports 126 and the outlet ports 128 (and/or the inlet ports and outlet ports themselves) are opened and fluid is pumped from the receptacles 130 connected to the inlet ports 126, through the inlet ports 126, and out through the outlet ports 128 and the lower ends of the capillary tubes 10. The channel 108 in the upper buffer chamber 100 and the capillary tubes 10 are then refilled with fluid by closing the electromagnetic valve 136 connected to the outlet port 128 (and/or the outlet port itself) while pumping the fluid from the receptacles 130 connected to the inlet ports 126 into the inlet ports 126 until the channel 108 in the upper buffer chamber 100 and the insides of the capillaries 10 have been filled with fluid. If desired, the emptying and refilling of the channel in the upper buffer chamber and the capillary tubes may be under the control of a computer.

As shown in FIGS. 9 and 10, the capillaries 10 extend from the capillary guide 20 into the lower buffer chamber 102 (during electrophoresis of the sample) or into a standard 96 well or 384 well microtiter plate (during loading of the sample). During electrophoresis as well as during sample loading the lower portions of the capillaries 10 pass through a grid 140 having the structure shown in FIGS. 9, 10, 17, and 18. As best illustrated in the cross section of FIG. 18, the grid 140 comprises a body 188 having a plurality of apertures 144 therein sized for receiving the capillaries 10. For example, the apertures 144 may be 0.5 mm in diameter. The apertures 144 are arranged so as to permit their alignment over the wells 146 of a standard 96 well or 384 well microtiter plate 148. The body may comprise a pair of metallic plates 142 having a spacing section 150 therebetween. The spacing section has apertures 152 therein and is disposed between the metallic plates 142 such that the apertures 152 in the spacing section 150 are aligned with the apertures 144 in the metallic plates 142. Preferably, the spacing section 150 is made of a nonconducting elastic material such as rubber. The metallic plates 142 may be secured to one another using screws 154 located at the corners of the grid 140. The body 188 has a shoulder 190 which contacts the microtiter plate 148 to align the apertures 144 and 152 in the metallic plates and the spacer section with the wells in the microtiter plate 148. As shown in FIG. 18, during loading of the sample the capillaries 10 pass through the apertures 144 in the metallic plates 142 and the apertures 152 in the spacing section 150 such that they contact the sample in the wells 146 of the microtiter plate 148.

Figure 19:
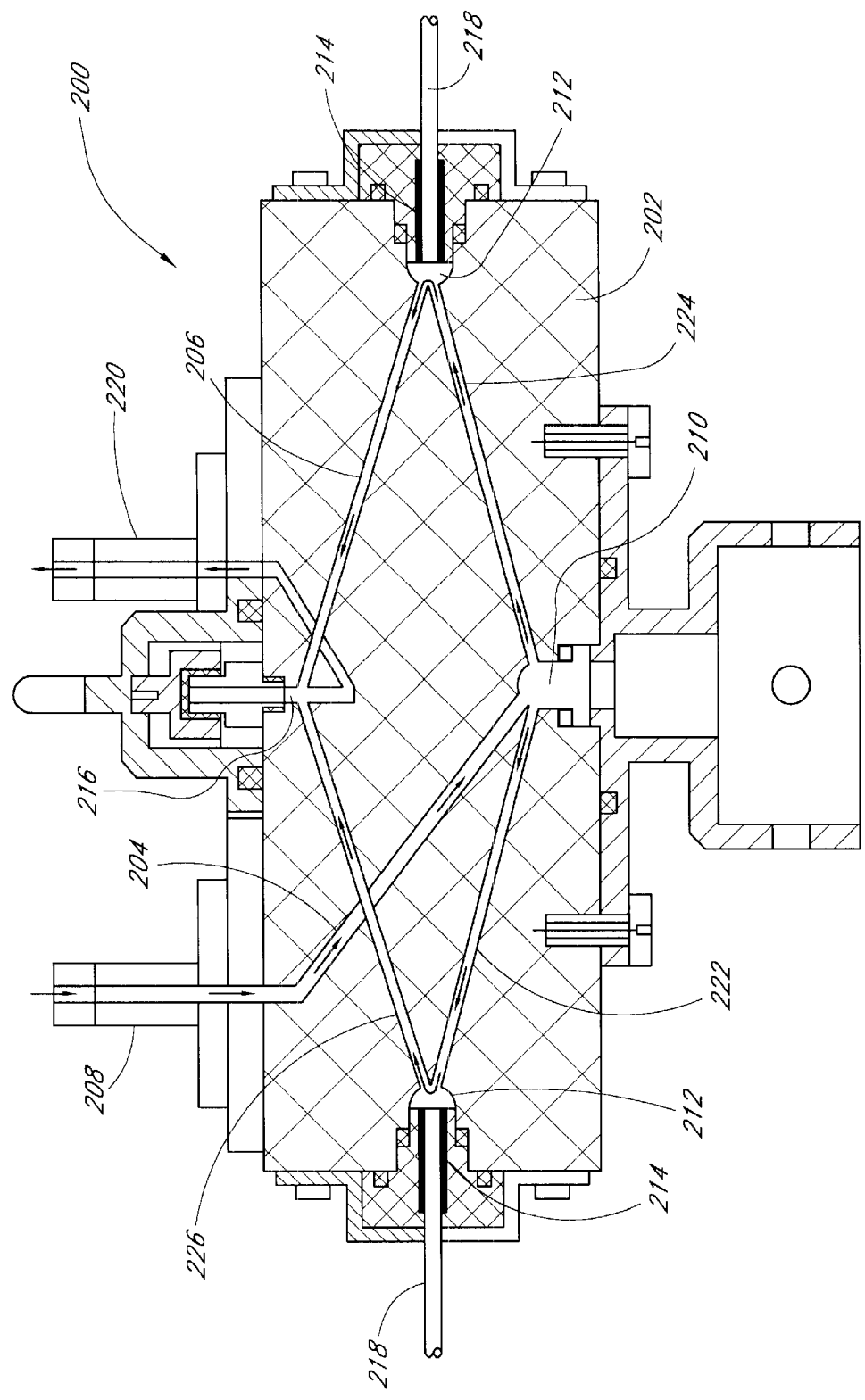
FIG. 19 is a cross section of an upper buffer chamber comprising a solid portion, at least one inlet channel, and at least one outlet channel.

In another embodiment the upper buffer chamber 200 comprises a solid portion. As shown in FIG. 19, which illustrates one version of this embodiment, the solid portion 202 comprises at least one inlet channel 204, 222, and 224, and at least one outlet channel 206, 226, and 228. In a preferred version of this embodiment the upper buffer chamber 200 is substantially solid, i.e. most of the volume of the upper buffer chamber is solid, thereby reducing the amount of electrophoresis buffer/separation medium which is required for an electrophoresis procedure.

Each inlet channel 204, 222, and 224 is in fluid communication with at least one inlet port 208. The inlet port 208 is in fluid communication with an inlet receptacle, such that fluid in the inlet receptacle can be directed through the inlet port 208 and into the inlet channel 204, 222, and 224. As illustrated for the embodiment of FIG. 10, high pressure pumps may be disposed between each inlet port 208 and the inlet receptacle. As illustrated for the embodiment of FIG. 10, electromagnetic valves are disposed between the inlet ports 208 and the inlet receptacles.

In the embodiment shown in FIG. 19, a plurality of inlet channels 204, 222, and 224 radiate from a central inlet member 210. Fluid introduced from inlet port 208 flows into an inlet channel 204 disposed between the inlet port and the central inlet member 210. The fluid from the central inlet member 210 flows into additional inlet channels 222 and 224, which are disposed between the central inlet member 210 and caps 212 positioned over adapters 214 at the ends of the capillary bundles.

In the embodiment illustrated in FIG. 19 a plurality of outlet channels 206 and 226 radiate from a central outlet member 216. The plurality of outlet channels 206 and 226 are disposed between the central outlet member 216 and the caps 212.

During washing of the upper buffer chamber, the inlet ports 208 and outlet ports 220 are open. If the buffer/separation medium is low in viscosity, the wash may be performed at low pressure using any desired wash solution, including water or buffered solutions. If the buffer/separation medium has high viscosity, the wash is performed at high pressure. Again, any desired wash solution may be used, including water or buffered solutions.

During the washing procedure, fluid introduced from the inlet port 208 flows into the central inlet member 210. From the central inlet member 210, the fluid flows through additional inlet channels 222 and 224, into the caps 212. From the caps 212, the fluid flows into the outlet channels 206 and 226. From the outlet channels 206 and 226, the fluid flows into the central outlet member 216, out the outlet port 220 and into the outlet receptacle. Fluid flow from one outlet channel 206 to outlet channel 226, for example, is prevented by the pressure at which the wash solution is provided as well as the fact that, since the central outlet member 216 has a greater diameter than the outlet channels 206 and 226, fluid will preferentially enter the central outlet member 216. As illustrated in the embodiment of FIG. 10, electromagnetic valves may be disposed between the outlet ports 220 and the outlet receptacles. The direction of fluid flow during a wash procedure is indicated by the arrows in FIG. 19.

During the capillary refilling procedure, the inlet ports 208 are open, while the outlet ports 220 are closed. Fluid introduced from the inlet port 208 flows into the central inlet member 210. From the central inlet member 210, the fluid flows through additional inlet channels 222 and 224, into the caps 212. From the caps 212, the fluid flows into capillaries 218, forcing the used electrophoresis/separation medium out of the capillaries 218 and refilling the capillaries 218 with new electrophoresis/separation medium.

The embodiment of FIG. 19 is highly effective at removing gel particles adhering to the upper buffer chamber walls. In addition, since it does not contain a channel, the embodiment of FIG. 19 requires a smaller amount of electrophoresis/separation buffer than the embodiments of FIGS. 11–15. Furthermore, the embodiment of FIG. 19 facilitates the maintenance of high pressure within the upper buffer chamber and capillaries, since it contains less open space than the embodiments of FIGS. 11–15.

Figure 17:
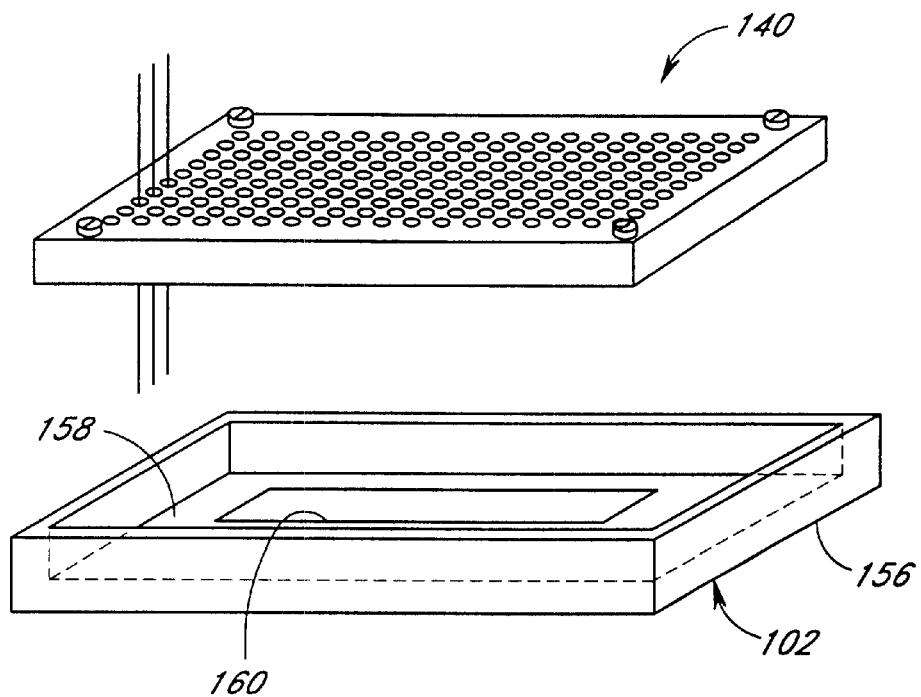
FIG. 17 is a perspective view of the lower buffer chamber and the grid.
Figure 18:
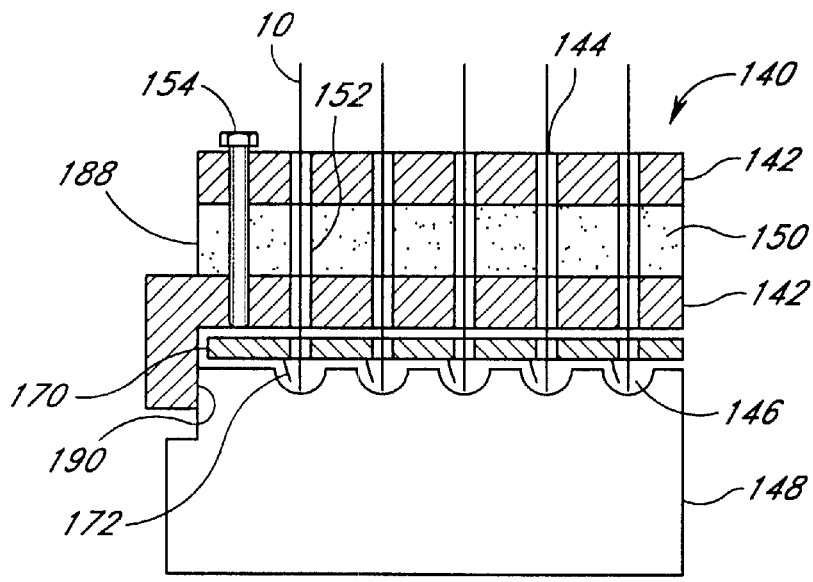
FIG. 18 is a cross section of the grid of FIG. 13 positioned above a microtiter plate.

As shown in FIGS. 9, 10 and 17 during electrophoresis the grid 140 is placed over the lower buffer chamber 102 such that the lower ends of the capillaries contact buffer solution in the lower buffer chamber. The lower buffer chamber 102 may be a rectangular base 156 having a cavity 158 therein for receiving the buffer. A conductor 160 runs along the periphery of the rectangular base 156. The conductor 160 is connected to the voltage source 162. In the stationary optical path embodiment of FIG. 9, the conductor 160 may be connected to the voltage source 162 through a contact (not shown) on the bottom of the lower buffer chamber 102. The contact is electrically connected to the voltage source 162. In the rotating optical path embodiment of FIG. 10, conductor 160 may be connected to the voltage source 162 through a connector (not shown) on the side of the lower buffer chamber 102.

Alternatively, the lower buffer chamber may comprise the grid 140 with the conducting plate 170 as illustrated in FIG. 18. Briefly, after loading the samples as described below, the wells 146 in the microtiter plate 148 are filled with electrophoresis buffer. The conducting plate 170 is placed beneath the spacing section 150, such that the leads 172 extend into the wells 146 of the microtiter plate 148. The conducting plate 170 is connected to the voltage source.

Thus, when the channel 108 in the upper buffer chamber 100 is filled with electrophoresis/separation buffer, a continuous electrical circuit exists between the lower buffer chamber 102 and the upper buffer chamber 100 such that samples loaded in the lower ends of the capillaries 10 can migrate from the lower end of the capillaries to the upper end of the capillaries when a potential difference is applied between the lower buffer chamber 102 and the upper buffer chamber 100.

Use of the present invention for obtaining the sequence of a plurality of DNA samples will now be described.

The channel 108 in the upper buffer chamber 100 and the capillaries 10 are filled with a suitable electrophoresis buffer/separation medium as described above. Preferably, both the electrophoresis buffer and the separation medium comprise a solution of a soluble cellulose derivative. More preferably, the solution of the soluble cellulose derivative which is used both as the electrophoresis buffer and as the separation medium comprises 7M urea, 1×TBE, and 2.7% hydroxypropyl methylcellulose. In other embodiments, the electrophoresis buffer and separation medium may comprise polyethylene glycol (PEG), polyethylene oxide (PEO) or hydroxyethyl cellulose. Alternatively, the separation medium may comprise polyacrylamide gels, including linear polyacrylamide gels, or gels such as those described in Swerdlow et al., Anal. Chem. 63:2835–2841, 1991, WO 94/29712, and Huang et al., Anal. Chem. 64:967–972 (1992), the disclosures of which are incorporated herein by reference.

DNA sequencing reactions are performed using conventional techniques such as those described in Huang et al., Anal. Chem. 64:967–992,1992; Quesada et al., Biotechniques 10:616–625, 1991; Swerdlow et al., Anal. Chem. 63:2835–2841, 1991, the disclosures of which are incorporated herein by reference. For example, the DNA sequencing techniques used to generate the substrates for sequence determination may comprise the four spectral channel, two spectral channel or one spectral channel techniques described in Swerdlow et al., Anal. Chem. 63:2835–2841, 1991.

Preferably, the four spectral channel technique is used. Briefly, in this technique, our labeling reactions for each DNA sample to be sequenced are performed on a primer which is capable of hybridizing to the DNA in the sample. In each of the four labeling reactions, a different fluorescent label having a different fluorescence pattern is used to label the primer. The fluorescent label may comprise any of the fluorescent labels conventionally employed for DNA sequencing, including FAM, JOE, TAMRA, and ROX.

A separate extension and dideoxynucleotide termination reaction is then performed for each of the four hybridized primers, such that the reaction products for each labeled primer terminate at one of the four nucleotides found in the DNA sequence. The products of the sequencing reactions are desalted and pooled and placed into the sample wells of the 96 or 384 well microtiter plate. Alternatively, if desired, the products of each sequencing reaction may each be placed in separate wells of the microtiter plate.

The grid 140 is secured to the microtiter plate 148 such that the lower ends of the capillary tubes 10 contact the sequencing reaction products in the wells 146. As shown in FIG. 18, a conducting plate 170 may be disposed between the lower metallic plate 142 of the grid 140 and the microtiter plate 148. The conducting plate 170 has short platinum leads 172 thereon which extend into the sample solution in the wells 146. The sequencing reaction products in the wells of the microtiter plate 148 are injected into the capillaries 10 by applying a voltage of between about 3 and about 15 kV, preferably 8 kV to the conducting plate for a period of 10–20 seconds or more.

Alternatively, rather than using the grid 140 and conducting plate 170 during sample loading, a metallic microtiter plate may be used. In this procedure, voltage is applied to the microtiter plate during sample loading.

Following injection of the samples, the grid 140 is placed over the lower buffer chamber 102 containing 1×TBE, 1.2% hydroxypropylmethylcellulose such that the lower ends of the capillaries 10 contact the buffer solution. Electrophoresis is conducted at a voltage of 12 kV for a period of 2 hours. Samples are read as they pass through the detection region of the capillary tubes. In those embodiments in which the electrophoresis system is thermoisolated, the temperature of the electrophoresis may be maintained between 30 degrees Celsius and 80 degrees Celsius. Preferably, the temperature is maintained at 50 degrees Celsius. Temperature regulation may be controlled by a computer 42 connected to a temperature regulator 166.

It will be appreciated that while the above examples describe the use of the present devices for DNA sequencing, the device may also be used in a variety of other applications. For example, the device may be used to sequence macromolecules other than DNA, including polysaccharides.

The present device may also be used to determine whether a subject contains an allelic variation known to confer a particular phenotype, such as a genetic disease. In this application, a DNA sample is obtained from the subject. The DNA is denatured and hybridized to a primer known to hybridize in the region adjacent to the allelic variation known to confer the phenotype of interest. Extension and termination reactions are performed as described above to determine whether the subject carries the allele of interest. Using the present device, DNA samples from a single patient can be analyzed for a plurality of allelic variations. In addition, the present device may be used to analyze DNA samples from numerous subjects to determine whether the subjects carry one or more allelic variations of interest.

The present device may also be used for minisequencing, genotyping, differential gene expression analyses, sizing nucleic acids or other compounds, or fast spectral analysis of biochemical reactions containing fluorophores.

It will be appreciated that no matter how detailed the foregoing appears in text, the invention can be practiced in many ways. As is also stated above, it should further be noted that the use of particular terminology when describing certain features or aspects of the present invention should not be taken to imply that the broadest reasonable meaning of such terminology is not intended, or that the terminology is being re-defined herein to be restricted to including any specific characteristics of the features or aspects of the invention with which that terminology is associated. Thus, although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims and any equivalents thereof. All documents cited herein are incorporated herein by reference in their entirety.

What is claimed is:

1. An apparatus comprising:
   a first buffer chamber comprising a solid portion, a plurality of inlet channels in said solid portion, and a plurality of outlet channels in said solid portion, wherein said plurality of inlet channels are in fluid communication with at least one inlet port, said plurality of outlet channels are in fluid communication with at least one outlet port, and each of said plurality of inlet channels is in fluid communication with at least one outlet channel; and
   a plurality of capillaries arranged in a plurality of capillary bundles, each of said plurality of capillaries having a first end, a second end, and an intermediate portion disposed between said first end and said second end, wherein said first end of each of the capillaries in each of said capillary bundles extends into fluid communication with said first buffer chamber and is in fluid communication with at least one of said plurality of inlet channels such that fluid can enter said first end of each of said capillaries through said at least one of said plurality of inlet channels and wherein said first end of each of said capillaries is also in fluid communication with at least one of said plurality of outlet channels such that fluid can exit from said first buffer chamber via at least one of said plurality of outlet channels.

2. The apparatus of claim 1, further comprising a second buffer chamber, wherein said second end of each of the capillaries in each of said capillary bundles extends into fluid communication with said second buffer chamber.

3. The apparatus of claim 2 further comprising an inlet receptacle in fluid communication with said inlet port and an outlet receptacle in fluid communication with said outlet port.

4. The apparatus of claim 2, wherein said second buffer chamber comprises a grid, said grid comprising:
   a body having apertures therein, said apertures being sized for receiving capillaries therein and configured such that said apertures align with the wells in a microtiter plate when said body is placed over a microtiter plate; and
   a reservoir for holding electrophoresis medium.

5. The apparatus of claim 4, wherein said reservoir for holding electrophoresis medium comprises a microtiter plate and said grid further comprises a conducting plate positioned between said body and said microtiter plate, said conducting plate having leads thereon which extend into the wells of said microtiter plate.

6. The apparatus of claim 1, further comprising at least one cap positioned over said first end of each of said plurality of capillaries in each of said plurality of capillary bundles, wherein at least one inlet channel and at least one outlet channel meet at said at least one cap, and wherein said at least one cap permits fluid flow from at least one inlet channel into at least one outlet channel during washing procedures, and wherein said at least one cap permits fluid flow through said plurality of capillaries during filling/refilling procedures.

7. The apparatus of claim 6, wherein said plurality of inlet channels radiate from a central inlet member and said plurality of outlet channels radiate from a central outlet member.

8. The apparatus of claim 1, wherein the intermediate portions of said plurality of capillaries intersect a plane perpendicular to said intermediate portions such that a curving contour is formed by the intersection points of said intermediate portions of each of said plurality of capillaries with said plane.

9. The apparatus of claim 8 wherein said curving contour is substantially closed.

10. The apparatus of claim 9 wherein said curving contour forms at least a portion of a circle.

11. The apparatus of claim 10, wherein said plurality of capillaries form a substantially cylindrical array of capillaries.

12. The apparatus of claim 11, further comprising an illuminator positioned inside of said substantially cylindrical array of capillaries.

13. The apparatus of claim 12, wherein said illuminator is rotatable such that said illuminator sequentially illuminates each capillary in said plurality of capillaries.

14. The apparatus of claim 13, further comprising a synchronization detector for obtaining data from said capillaries in response to a signal indicating that said capillaries are in focus.

15. The apparatus of claim 14, wherein said synchronization detector comprises a photodetector.

16. The apparatus of claim 11, further comprising an illuminator positioned outside of said substantially cylindrical array of capillaries.

17. The apparatus of claim 16, wherein said substantially cylindrical array of capillaries is rotatable such that each capillary in said plurality of capillaries is sequentially illuminated by said illuminator.

18. The apparatus of claim 17, further comprising a synchronization detector for obtaining data from said capillaries in response to a signal indicating that said capillaries are in focus.

19. The apparatus of claim 18, wherein said synchronization detector comprises a photodetector.

20. The apparatus of claim 18, further comprising a trigger for providing a signal to the synchronization detector indicative of the beginning of a new scanning cycle.

21. The apparatus of claim 14, further comprising a trigger for providing a signal to the synchronization detector indicative of the beginning of a new scanning cycle.

22. The apparatus of claim 1 further comprising a light collector for detecting light emitted by substances within said capillaries, wherein said light collector comprises a spectral separator and at least one charge coupled device.

23. A method of performing electrophoresis comprising:
   obtaining an electrophoresis device comprising:
      a first buffer chamber comprising a solid portion, a plurality of inlet channels in said solid portion, and a plurality of outlet channels in said solid portion, wherein said plurality of inlet channels are in fluid communication with at least one inlet port, said plurality of outlet channels are in fluid communication with at least one outlet port, and each of said plurality of inlet channels is in fluid communication with at least one outlet channel; and
      a plurality of capillaries arranged in a plurality of capillary bundles, each of said plurality of capillaries having a first end, a second end, and an intermediate portion disposed between said first end and said second end, wherein said first end of each of the capillaries in each of said capillary bundles extends into fluid communication with said first buffer chamber and is in fluid communication with at least one of said plurality of inlet channels such that fluid can enter said first end of each of said capillaries through said at least one of said plurality of inlet channels and wherein said first end of each of said capillaries is also in fluid communication with at least one of said plurality of outlet channels such that fluid can exit from said first buffer chamber via at least one of said plurality of outlet channels;
      automatically directing an electrophoresis buffer/separation medium from said at least one inlet port into said first end of each of the capillaries in each of said capillary bundles such that each of said capillaries becomes filled with said electrophoresis/separation medium; and
   performing electrophoresis on samples introduced into each of the capillaries.

24. The method of claim 23, further comprising washing said upper buffer chamber by automatically directing a wash solution into said at least one inlet port, from said at least one inlet port into said plurality of inlet channels, and from said plurality of inlet channels through said plurality of outlet channels and out said at least one outlet port.

25. The method of claim 24, further comprising opening said at least one inlet port and said at least one outlet port during said washing procedure.

26. The method of claim 24, further comprising refilling said capillaries with said electrophoresis/separation medium by automatically directing an electrophoresis buffer/separation medium from said at least one inlet port into said first ends of said capillaries such that said capillaries become filled with said electrophoresis/separation medium.

27. The method of claim 26, further comprising opening said inlet port during said refilling procedure and closing said outlet port during said refilling procedure.

28. The method of claim 23, wherein said step of performing electrophoresis comprises:
   placing samples into wells in a microtiter plate;
   positioning a grid having apertures therein over said microtiter plate such that said capillaries extend through said apertures and into said wells of said microtiter plate; and
   applying a voltage between said first buffer chamber and said second buffer chamber such that said samples move from said wells of said microtiter plate into said capillaries.

29. The method of claim 28, wherein said grid further comprises a conducting plate having leads extending therefrom between said grid and said microtiter plate such that said leads extend into said microtiter plate.

30. The method of claim 29, further comprising filling said wells of said microtiter plate with electrophoresis buffer after said samples have entered said capillaries.

31. An apparatus comprising:
   a first buffer chamber comprising a solid portion, at least one inlet channel in said solid portion, and at least one outlet channel in said solid portion, wherein said at least one inlet channel is in fluid communication with at least one inlet port, said at least one outlet channel is in fluid communication with at least one outlet port and said at least one inlet channel is in fluid communication with said at least one outlet channel; and
   a plurality of capillaries having first ends, second ends, and intermediate portions disposed between said first ends and said second ends, wherein said first ends extend into fluid communication with said first buffer chamber and are in fluid communication with said at least one inlet channel such that fluid can enter said first ends through said at least one inlet channel and wherein said first ends are also in fluid communication with said at least one outlet channel such that fluid can exit from said first buffer chamber via said at least one outlet channel;
   wherein the intermediate portions of said plurality of capillaries intersect a plane perpendicular to said intermediate portions such that a substantially circular contour is formed by the intersection points of said intermediate portions of each of said plurality of capillaries with said plane; and
   a detector for sequentially obtaining data from each of said capillaries.

32. The apparatus of claim 31, further comprising a second buffer chamber, wherein said second ends of said capillaries extend into fluid communication with said second buffer chamber.

33. The apparatus of claim 32, further comprising an inlet receptacle in fluid communication with said inlet port and an outlet receptacle in fluid communication with said outlet port.

34. The apparatus of claim 32, wherein said second buffer chamber comprises a grid, said grid comprising:
   a body having apertures therein, said apertures being sized for receiving capillaries therein and configured such that said apertures align with the wells in a microtiter plate when said body is placed over a microtiter plate; and
   a reservoir for holding electrophoresis medium.

35. The apparatus of claim 34, wherein said reservoir for holding electrophoresis medium comprises a microtiter plate and said grid further comprises a conducting plate positioned between said body and said microtiter plate, said conducting plate having leads thereon which extend into the wells of said microtiter plate.

36. The apparatus of claim 31, further comprising at least one cap positioned over said first ends of said capillaries, wherein said at least one inlet channel and said at least one outlet channel meet at said at least one cap, and wherein said at least one cap permits fluid flow from at least one inlet channel into at least one outlet channel during washing procedures, and wherein said at least one cap permits fluid flow through said plurality of capillaries during filling/refilling procedures.

37. The apparatus of claim 36, wherein said apparatus has a plurality of inlet channels radiating from a central inlet member and a plurality of outlet channels radiating from a central outlet member.

38. The apparatus of claim 31, wherein the intermediate portions of said plurality of capillaries intersect a plane perpendicular to said intermediate portions such that a curving contour is formed by the intersection points of said intermediate portions of each of said plurality of capillaries with said plane.

39. The apparatus of claim 38, wherein said curving contour is substantially closed.

40. The apparatus of claim 39, wherein said curving contour forms at least a portion of a circle.

41. The apparatus of claim 40, wherein said plurality of capillaries form a substantially cylindrical array of capillaries.

42. The apparatus of claim 41, further comprising an illuminator positioned inside of said substantially cylindrical array of capillaries.

43. The apparatus of claim 42, wherein said illuminator is rotatable such that said illuminator sequentially illuminates each capillary in said plurality of capillaries.

44. The apparatus of claim 43, further comprising a synchronization detector for obtaining data from said capillaries in response to a signal indicating that said capillaries are in focus.

45. The apparatus of claim 44, wherein said synchronization detector comprises a photodetector.

46. The apparatus of claim 44, further comprising a trigger for providing a signal to the synchronization detector indicative of the beginning of a new scanning cycle.

47. The apparatus of claim 41, further comprising an illuminator positioned outside of said substantially cylindrical array of capillaries.

48. The apparatus of claim 47, wherein said substantially cylindrical array of capillaries is rotatable such that each capillary in said plurality of capillaries is sequentially illuminated by said illuminator.

49. The apparatus of claim 48, further comprising a synchronization detector for obtaining data from said capillaries in response to a signal indicating that said capillaries are in focus.

50. The apparatus of claim 49, wherein said synchronization detector comprises a photodetector.

51. The apparatus of claim 49, further comprising a trigger for providing a signal to the synchronization detector indicative of the beginning of a new scanning cycle.

52. The apparatus of claim 31, further comprising a light collector for detecting light emitted by substances within said capillaries, wherein said light collector comprise a spectral separator and at least one charge coupled device.

53. The apparatus of claim 31, further comprising:
   a plurality of inlet channels in said solid portion, and
   a plurality of outlet channels in said solid portion, wherein said plurality of inlet channels are in fluid communication with said at least one inlet port, said plurality of outlet channels are in fluid communication with said at least one outlet port, and each of said plurality of inlet channels is in fluid communication with at least one outlet channel;
   wherein said capillaries are arranged in a plurality of capillary bundles, each of said plurality of capillaries having a first end, a second end, and an intermediate portion disposed between said first end and said second end, wherein said first end of each of the capillaries in each of said capillary bundles extends into fluid communication with said first chamber and is in fluid communication with at least one of said plurality of inlet channels such that fluid can enter said first end through said plurality of inlet channels and wherein said first end is also in fluid communication with at least one of said plurality of outlet channels such that fluid can exit from said first buffer chamber via at least one of said plurality of outlet channels.

54. A method of performing electrophoresis comprising:
   obtaining an electrophoresis device comprising:
     a first buffer chamber comprising a solid portion, at least one inlet channel in said solid portion, and at least one outlet channel in said solid portion, wherein said at least one inlet channel is in fluid communication with at least one inlet port, said at least one outlet channel is in fluid communication with at least one outlet port and said at least one inlet channel is in fluid communication with said at least one outlet channel; and
     a plurality of capillaries having first ends, second ends, and intermediate portions disposed between said first ends and said second ends, wherein said first ends extend into fluid communication with said first buffer chamber and are in fluid communication with said at least one inlet channel such that fluid can enter said first ends through said at least one inlet channel and wherein said first ends are also in fluid communication with said at least one outlet channel such that fluid can exit from said first buffer chamber via said at least one outlet channel; and
     wherein the intermediate portions of said plurality of capillaries intersect a plane perpendicular to said intermediate portions such that a substantially circular contour is formed by the intersection points of said intermediate portions of each of said plurality of capillaries with said plane;
   automatically directing an electrophoresis buffer/separation medium from said at least one inlet port into said first end of each of said plurality of capillaries such that each of said plurality of capillaries becomes filled with said electrophoresisl-separation medium; and
   performing electrophoresis on samples introduced into each of said plurality of capillaries.

55. An apparatus comprising:

a first buffer chamber comprising a solid portion, a plurality of inlet channels in said solid portion, and a plurality of outlet channels in said solid portion, wherein said plurality of inlet channels are in fluid communication with at least one inlet port, said plurality of outlet channels are in fluid communication with at least one outlet port, and each of said plurality of inlet channels is in fluid communication with at least one outlet channel;

a plurality of capillaries each of said plurality of capillaries having a first end, a second end, and an intermediate portion disposed between said first end and said second end, wherein said first end extends into fluid communication with said first buffer chamber and is in fluid communication with at least one of said plurality of inlet channels such that fluid can enter said first end through said plurality of inlet channels and wherein said first end is also in fluid communication with at least one of said plurality of outlet channels such that fluid can exit from said first buffer chamber via at least one of said plurality of outlet channels;

a detector for sequentially obtaining data from each of said capillaries; and wherein said intermediate portions are arranged to form a substantially cylindrical array of capillaries, and wherein said detector and said array are configured to rotate relative to one another.

* * * * *